United States Patent [19]

Webb, Jr.

[11] 4,218,575
[45] Aug. 19, 1980

[54] ALKYLATION EFFLUENT FLASH VAPORIZATION WITH HEAT RECOVERY

[75] Inventor: Orlando Webb, Jr., Lee's Summit, Mo.

[73] Assignee: Stratford/Graham Engineering Corporation, Kansas City, Mo.

[21] Appl. No.: 894,996

[22] Filed: Apr. 10, 1978

[51] Int. Cl.² .................................................. C07C 3/54
[52] U.S. Cl. ...................................... 585/715; 585/719; 585/723; 585/730
[58] Field of Search .................... 260/683.59, 683.62, 260/683.48, 683.43, 683.4 F, 683.58; 585/715, 719, 723

[56] References Cited

U.S. PATENT DOCUMENTS

| | | | |
|---|---|---|---|
| Re. 26,060 | 7/1966 | Nathan | 260/683.59 |
| 2,281,248 | 4/1942 | Putney | 260/683.43 |
| 2,320,199 | 5/1943 | Sellmeyer | 260/683.59 |
| 2,334,955 | 11/1943 | Putney | 260/683.59 |
| 2,986,590 | 5/1961 | Knoble et al. | 260/683.59 |
| 3,068,308 | 12/1962 | Stiles | 260/683.59 |
| 3,105,102 | 9/1963 | Webb, Jr. | 260/683.59 |
| 3,162,694 | 12/1964 | Beavon | 260/683.62 |
| 3,175,023 | 3/1965 | Gross et al. | 260/683.59 |
| 3,215,752 | 11/1965 | Vermilion, Jr. | 260/683.59 |
| 3,415,899 | 12/1968 | VanDijk | 260/683.62 |
| 3,580,962 | 5/1971 | Moorer et al. | 260/683.62 |
| 4,128,597 | 12/1978 | Jones | 260/683.62 |

Primary Examiner—George Crasanakis
Attorney, Agent, or Firm—Thomas M. Scofield

[57] ABSTRACT

Improvements in alkylation effluent flash vaporization systems used in processes of alkylating isoparaffinic hydrocarbons with olefinic hydrocarbons in the presence of acid catalyst and an excess of isoparaffinic hydrocarbons; improvements in heat sources used in such alkylation effluent flash vaporization systems, specifically utilizing hot and compressed isoparaffinic hydrocarbon vapors generally available in such systems from such sources as fractionation (deisobutanizer) overhead or vapor flashing processes utilized in cooling the reaction step or both; improvements in alkylation effluent flash vaporization systems which reduce the load on the conventional step of retrieving excess isoparaffinic hydrocarbons from the alkylation reaction effluent for recycle to the reaction step.

27 Claims, 6 Drawing Figures

ALKYLATION EFFLUENT FLASH VAPORIZATION WITH HEAT RECOVERY

BACKGROUND OF THE INVENTION

Many conventional alkylation methods and processes are known and employed, varying more or less from one another, wherein isobutane is alkylated with olefins in the presence of sulphuric acids or other acid catalyst and an excess of isobutane. Several types of reaction vessels may be employed in these processes. The reaction steps of the several processes is typically cooled by indirect or direct heat exchange to control reaction temperature. Where the reaction step is heat exchanged, closed cycle refrigeration, effluent refrigeration or direct vaporization of reacting liquids may or may not be employed in a specific case.

In each of the typical and conventional alkylation processes, however, whatever the specific arrangements for conducting the reaction may be, or heat exchanging it, once the catalyst phase has been separated from the hydrocarbon phase of the reaction step effluent, the hydrocarbon component is typically passed to various stages of fractionation where alkylate product is separated from excess isoparaffinic hydrocarbons, in order that the latter may be recycled as feed to the reaction step to aid in the important goal and step of maintenance of a large proportional excess of isobutane in the reaction step.

The equipment involved in such fractionation separation typically includes a deisobutanizer tower of great expense and size. For example, an 8,000 barrel of product per day tower today has a cost in excess of $800,000. In view of such great cost it is eminently desirable to reduce the size of the deisobutanizer tower as much as possible. However, any change in this direction lies directly in the face of one of the most important functions of the fractionation system, specifically, to return as much isobutane as possible to the reaction step in order to maintain the optimum reaction conditions and produce the highest quality alkylate product.

Another important consideration in existing alkylation plants is how to increase the capacity of an existing plant by addition of one or more reaction vessels with a concomitant investment in as little additional fractionation equipment as possible. Once again, when the quantity of hydrocarbon phase effluent is increased, the requirement of separation of isoparaffinic hydrocarbons therefrom is also additionally increased. This generally means proportional addition of expensive fractionation equipment at great expense in time, cost, space and the like.

My U.S. Pat. No. 3,055,958 "Alkylation Effluent Flash Vaporization System", issued Sept. 25, 1962 shows effective means, apparatus and methods for meeting major aspects of the problems stated. Specifically, by use of my alkylation effluent flash vaporization process and apparatus prior to the fractionation steps, a substantial and important portion of the isoparaffinic hydrocarbons in the net hydrocarbon phase effluent from the reaction step is returned to the reaction step without reaching the fractionation stages. The methods disclosed in that Patent were adequate for their time with respect to obtaining the goals and objects related in that Patent and meeting the problems outlined above. However, in the present day and age, with the great cost of energy a reality for the present and foreseeable future, improved modes of carrying out alkylation effluent flash vaporization systems are called for. Specifically, the economics of steam as a heat exchanging medium available for use in such systems are very much in question. Accordingly, heat sources for use in the flash vaporization separation system must preferably be found of substantially different type to meet the needs of the present and future times.

OBJECTS OF THE INVENTION

Therefore, an object of the present invention is to provide substantial improvements in the alkylation effluent flash vaporization systems of the Webb U.S. Pat. No. 3,055,958, issued Sept. 25, 1962 for "Alkylation Effluent Flash Vaporization System".

Another object of the invention is to provide improved means and methods for reducing the load on both newly constructed and existing alkylation fractionation systems so that, in newly constructed alkylation systems, the deisobutanizer tower may be of markedly reduced size without reducing the quantity of isobutane recycled to the reaction and, with respect to already existent alkylation systems, the alkylate producing capacities may be greatly increased without, again, reducing the quantity of isobutane recycled to the reaction step or requiring additional fractionation tower construction or addition. Such should be the case without requiring original or increased steam supply as a heating source.

Another object of the invention is to provide improved heat sources for alkylation effluent flash vaporization systems used in reducing the load on alkylation fractionation systems, which new heat sources are of great simplicity, involve a minimum of expense to apply and, further, a minimum of plant redesign.

Another object of the invention is to provide new heat sources for alkylation effluent flash vaporization systems which may be applied to any existent alkylation systems, independent of the type of reaction vessel employed in the reaction step, whether or not the reaction step is heat exchanged, or how the reaction step is heat exchanged.

Another object of the invention is to provide an alkylation flash vaporization system particularly adapted to the hydrogen fluoride catalyzed alkylation system seen in the U.S. Pat. No. to D. A. Putney, 2,977,397 issued Mar. 28, 1961 for "Hydrogen Fluoride Alkylation With Effluent Refrigeration".

Another object of the invention is, in an alkylation reaction system, to utilize light hydrocarbon vapors from either the fractionation overhead or the reaction vessel heat exchange, or both, to heat exchange (heat) the net hydrocarbon phase effluent from the reaction step before such reaches the fractionation step by compressing such vapors to heat them to a substantial temperature differential over that of the net hydrocarbon phase effluent and passing one or both such vapors in indirect heat exchange with said effluent.

A particular object of the invention is to utilize light hydrocarbon vapors rich in isobutane generated from the heat exchange of an alkylation reaction step as at least one heat source for a flash vaporization system by compressing the vapors to heat them and then utilizing them as a heat exchanging medium in a vaporizing condenser through which passes some of the hydrocarbon phase effluent of the alkylation reaction to drive off vapors rich in isobutane from the said effluent, all of the isobutane rich vapors, including those used in the vaporizing condenser as heat exchanging medium and those driven off the hydrocarbon phase effluent being returned to the alkylation reaction step after condensation thereof.

Another object of the invention is to utilize light hydrocarbon vapors rich in isobutane taken off overhead from the distilling fractionation step of the deisobutanizer tower as at least part of the heat source for a flash vaporization system by compressing the said vapors to heat them and then utilizing them as a heat exchanging medium in a vaporizing condenser through which passes some of the hydrocarbon phase effluent of the alkylation reaction, thereby to drive off light hydrocarbon vapors rich in isobutane therefrom, all the light hydrocarbon vapors rich in isobutane from the deisobutanizer step and flash vaporization step being condensed and returned to the alkylation reaction step.

Another object of the invention is to utilize light heat exchanging medium vapors such as ammonia, freon or propane utilized in the closed cycle refrigeration of an alkylation reaction step (or the closed cycle refrigeration of light hydrocarbon vapors from an effluent flash drum in an alkylation reaction system utilizing hydrogen fluoride as a catalyst) as at least part of the heat source for a flash vaporization system associated with said alkylation reaction system by compressing the said vapors to heat them and then utilizing them as a heat exchanging medium in a vaporizing condenser through which passes some of the hydrocarbon phase effluent of the alkylation reaction, the condensed vapors then being returned to the closed cycle refrigeration system after such use.

THE DRAWINGS

In the drawings, embodiments of the invention are shown in the form of schematic flow diagrams illustrating a variety of alkylation systems and processes with the improvements applied thereto.

FIG. 1 STRUCTURE AND FUNCTION

Figure 1:
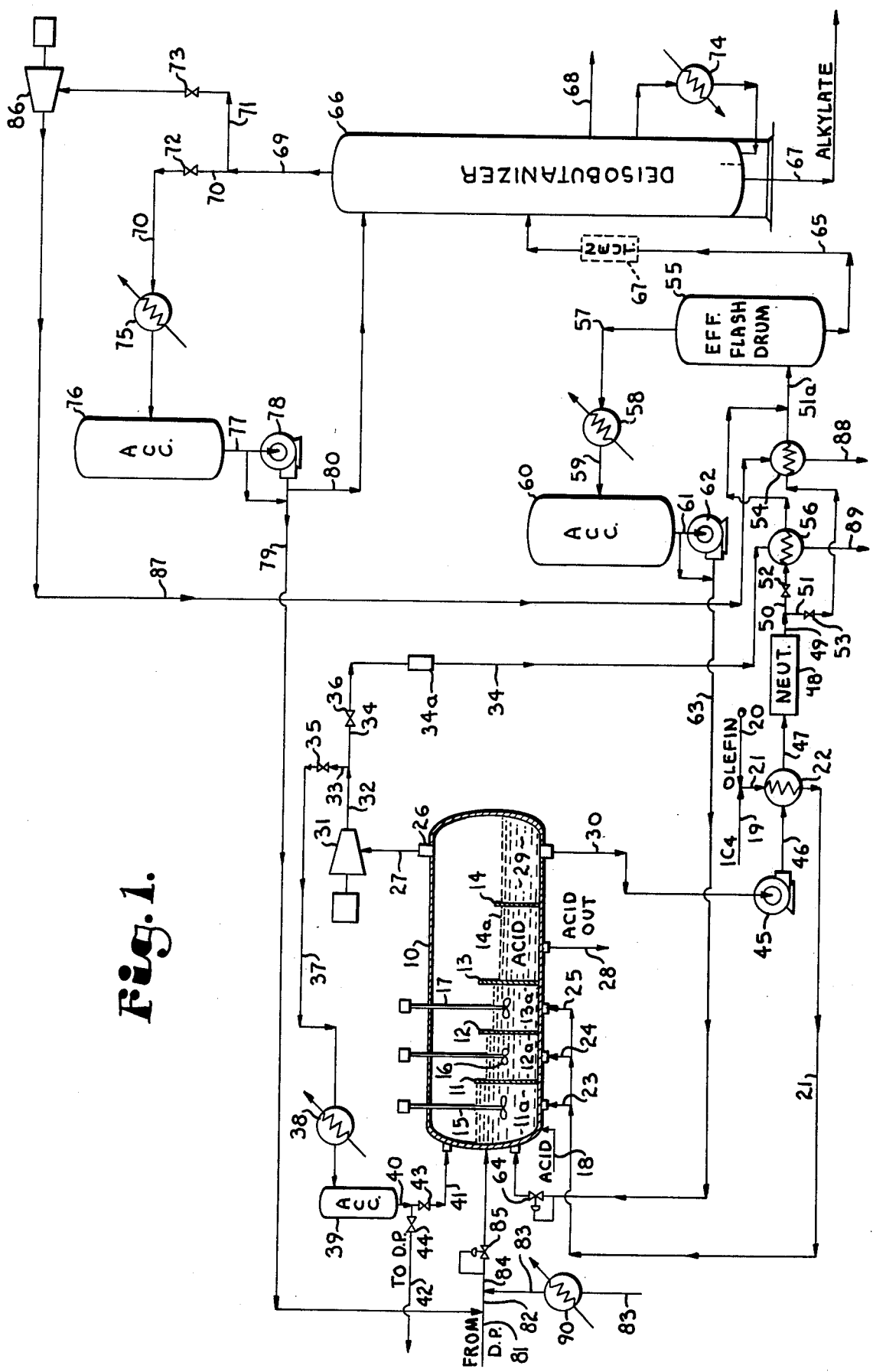
FIG. 1 is a schematic flow diagram illustrating an auto-refrigerated form of alkylation system.

Referring to FIG. 1, therein is shown the subject improvement illustrated as applied to an auto-refrigerated, cascade-type reactor installation. At 10 is shown the reactor vessel having height graded baffles 11, 12, 13 and 14 which operate to define a series of cascade flow chambers 11a, 12a, 13a and 14a therewithin. Mixer 15-17, inclusive agitate the liquid contents of the respective chambers. Flow line 18 supplies acid catalyst to chamber 11a. Fresh isobutane is supplied to the system through line 19. Olefin is supplied to the system through line 20, lines 19 and 20 joining in a common line 21 which is heat exchanged at 22, the mixed isobutane and olefin being supplied to chambers 11a-13a, inclusive through lines 23-25, inclusive. Flow control valves (not shown) preferably are provided on each of lines 23-25 inclusive.

The alkylation reaction takes place in chambers 11a-13a, inclusive, with light hydrocarbon vapors evolved withdrawn from fitting 26 at the top of vessel 10 through line 27. In chamber 14a, the acid settles and is taken out the bottom of the vessel through line 28. The spillover of hydrocarbon effluent from chamber 14a is taken off the bottom of the vessel from chamber 29 through line 30. Isobutane rich vapors taken off by line 27 pass to compressor 31 and thence to line 32 where the flow is selectively divided entirely between or split between lines 33 and 34 controlled by valves 35 and 36. Any flow through line 33 and valve 35 is passed via line 37 to condenser 38 and thence to accumulating vessel 39. Bottoms from accumulator 39, taken off through line 40, are split between lines 41 and 42 controlled by valves 43 and 44, respectively. Line 41 returns isobutane to the reactor and chamber 11a, while line 42 is a slip stream to a depropanizer (not seen). Valve 43 is preferably a back pressure valve. Booster compressor 34a is preferably provided on line 34 after valve 36 to compress and heat vapors rich in isobutane to the required heat content for effective heat exchange at vaporizer condenser 56.

The hydrocarbon effluent from chamber 29 passes through line 30 to pump 45, then through line 46 to heat exchanger 22, thereafter through line 47 to a neutralization step schematically indicated at 48. The neutralization system 48 may be a bauxite (dry) system or a more conventional caustic and water wash step (wet). Heat exchanger 22 operates to cool the isobutane and olefin input through line 21 to the reactor.

The output from neutralization step 48 is in line 49 which splits into lines 50 and 51 controlled by valves 52 and 53, respectively. Line 51 passes to heat exchange at 54 and thence to effluent flash drum 55. Line 50 passes to heat exchange at 56 and then joins line 51, making common line 51a prior to flash drum 55. The manner of heat exchange at 54 and 56 with respect to the paralleled flow of the hydrocarbon effluent from the neutralization step 48 will be later described in more detail.

At this point, suffice it to say that, due to heating at heat exchangers 54 and 56, isobutane rich vapors evolve from the net hydrocarbon effluent taken from chamber 29 through line 30. From effluent flash drum 55, line 57, off the top thereof, takes isobutane rich vapors, which condense at 58 and passes them via line 59 to accumulator drum 60. From accumulator 60, the condensed vapors are passed through line 61 and pump 62 into feed line 63 which leads into chamber 11a. Back pressure valve 64 may be employed on line 63 before input to chamber 11a.

Bottoms line 65 from effluent flash drum 55 passes the isobutane relieved net hydrocarbon effluent to deisobutanizer tower 66. At 67 is schematically indicated an alternative position for the neutralization step which, again, may be either dry or wet neutralization as previously described. Neutralization is placed either at 48 or 67 and is not employed in both places.

By providing the heat exchanging steps at 54 and 56, in connection with effluent flash drum 55, recycling light hydrocarbons back through condenser 58 and accumulator 60, I permit either initial reduction of the size of deisobutanizer tower 66 in a new system or greater capacity of an existent system of this type which already has a deisobutanizer tower of a fixed and given size. Accumulator 60 and/or pump 62 may not be necessary in some installations as, in many cases, the operating pressure of effluent flash drum 55 will be high enough to force the condensate back to the reactor without requiring a pump.

In the deisobutanizer tower 66, the net hydrocarbon effluent from chamber 29 of the auto-refrigerated reactor 10 is distilled, less light fraction vapors removed in effluent flash drum 55. Normal butane, alkylate and other hydrocarbons heavier than butane charged as part of the feed stock are withdrawn from the deisobutanizer through line 67. Alternatively, in conventional fashion, normal butane may be withdrawn intermediate the height of tower 66 through line 68. Any remaining isobutane and other light paraffinic hydrocarbon vapors are taken overhead through line 69 which splits into line 70 and 71 controlled by valves 72 and 73, respectively. Reboiling in conventional manner of the deisobutanizer tower is schematically shown at 74.

Vapors which are taken into line 70 through valve 72 are condensed at 75 and passed to accumulator 76. From accumulator 76 line 77 passes the liquid isobutane to pump 78 which feeds lines 70 and 80, valve controlled in conventional (not shown) fashion. Line 80 recycles liquid hydrocarbons to the deisobutanizer tower for reboiling, while line 79 recycles isobutane to join line 81 from a depropanizer, not shown. Common line 82 is joined by line 83, whose contents will be described. Common line 84 thereafter with back pressure valve 85 thereon feeds isoparaffinic hydrocarbons from numerous sources to be described to chamber 11a.

In the auto-refrigerated reaction vessel illustrated in FIG. 1, an important process equilibrium exists in the compartments of reactor 10. This equilibrium is affected by the olefin concentration in the acid in the compartments and the isobutane concentration of the hydrocarbon liquid with which it is in contact. Since isoparaffinic hydrocarbon vaporization takes place directly from the reaction zones in chambers 11a, 12a and 13a, the only isobutane (other than makeup) available to increase the concentration of isobutane in the liquid in contact with the catalyst is that which leaves the reactor as liquid effluent through line 30. Using a given deisobutanizer tower 66 and a given quantity of deisobutanizer overhead recycle, the effluent flash vaporization system shown and to be further described may be used to accomplish a considerable increase in isobutane concentration throughout the reaction and at the point of final equilibrium in the reactor, with a result that the yield and quality of the alkylate product will be increased.

The source of heat in heat exchanger 56 on line 50 is hot isobutane rich vapors from line 27 compressed in compressor 31 and passed to heat exchanger 56 through line 34. Line 34 can carry all or part of the isobutane rich vapors compressed at 31 to exchanger 56.

The source of heat for heat exchanger 54 in this system is hot, compressed isobutane rich vapors from tower 66. Line 71 can take all or part of the light vapors overhead from deisobutanizer 66 to compressor 86 with discharge line 87 passing to heat exchanger 54.

As previously mentioned, the net hydrocarbon effluent in line 49 after optional neutralization at 48 may be split entirely between either line 50 or 51 or evenly or in any desired ratio therebetween. That net hydrocarbon effluent passing through heat exchanger 56 is heated by hot, compressed light hydrocarbon vapors compressed in compressor 31, while the portion of the net hydrocarbon effluent passed through line 51 and exchanger 54 is heated by hot, compressed light hydrocarbon vapors taken off the overhead from deisobutanizer 66 and compressed in compressor 86. The hot vapors in lines 34 and 87 are at least mostly condensed in condensers 56 and 54, giving up their heat to the net hydrocarbon effluent quantities respectively going through the two heat exchangers. The discharge line from condenser 54 is 88, while the discharge line from condenser 56 is 89. These lines may be joined (not shown), but in any case pass to line 83 where additional heat exchange by cooling water takes place at 90 as required. This isobutane is then passed into line 84 and from thence into chamber 11a. Alternatively, one or both of lines 88 and 89 may pass to the reboiler of a depropanizer (not shown) for heating thereof (see FIG. 3) and cooling of more of the isobutane vapors compressed and heated at compressor 31 and/or compressor 86 (or further condensation thereof).

FIG. 2

Figure 2:
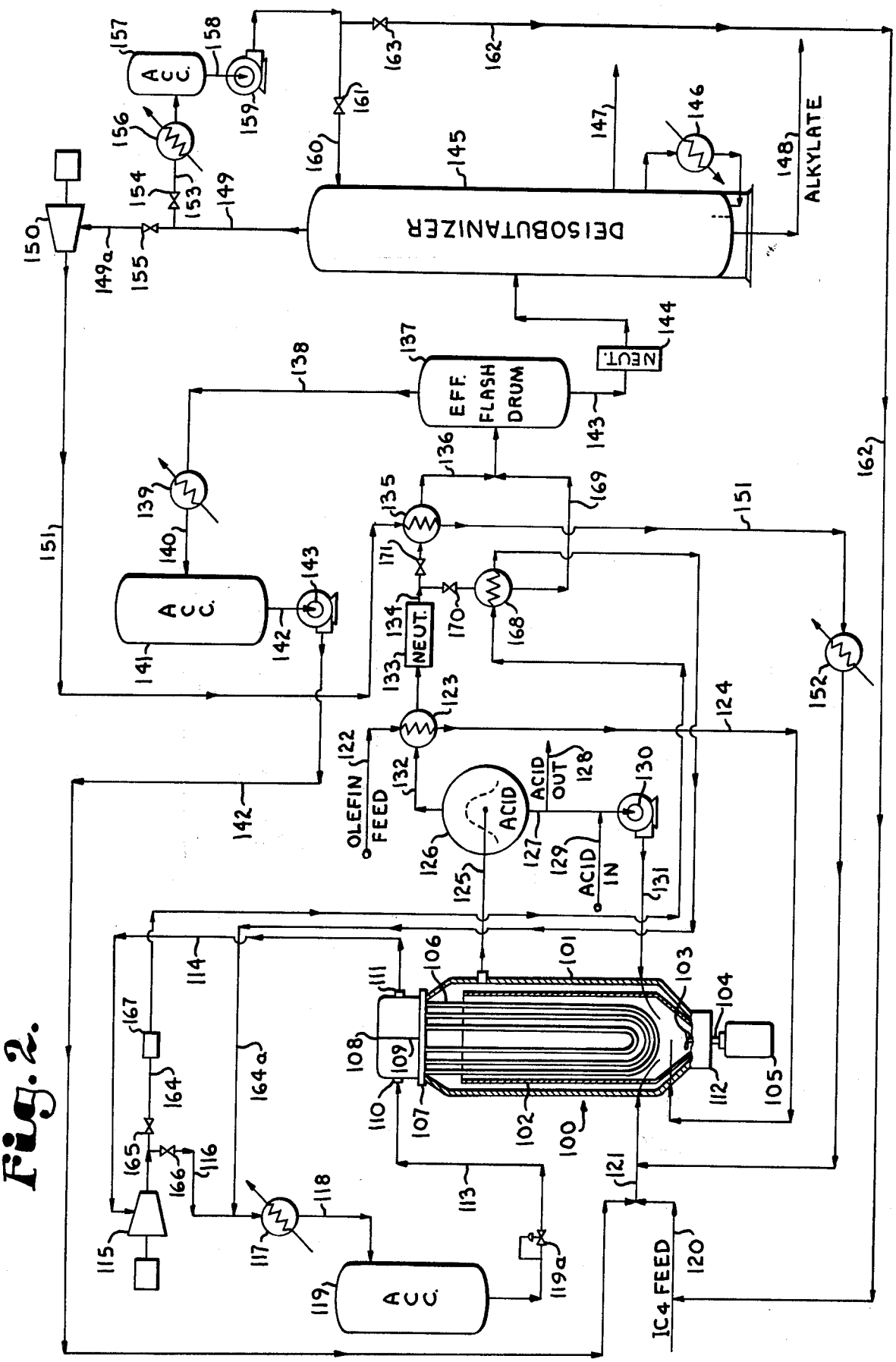
FIG. 2 is a schematic flow diagram showing an alkylation reaction system wherein the reaction step or vessel is heat exchanged by a closed cycled refrigeration system.

Referring now to FIG. 2, the numbering of this figure will start with 100 to avoid confusion with the preceding system. At 100 is generally designated a reaction vessel having an outer shell 101, a circulating tube 102 spaced inwardly from the outer shell and open at both ends to communicate with the space in the vessel. Impeller 103 is positioned at one end of circulating tube 102 and is driven by shaft 104 attached to motor or other prime mover 105. Heat exchanging tube bundle 106 comprises U-bends of tubing which are rolled into tube sheet 107. Header 108 has baffle 109 internally dividing its volume. Input and output connections 110 and 111 are positioned on the two sides of the header, leading into the separated spaces thereof.

Heat exchanging medium passing into fitting 110 goes into one side of header 108, thence into tubing 106 and thereafter out the other side of header 108 through fitting 111. The path of fluids in the reactor is through the center of the circulating tube from the heat exchanging tube bundle toward the impeller, into a circulating head 112 and out between the outside surface of circulating tube 102 and the inside surface of reactor shell 101. A typical reaction vessel of this type is seen in U.S. Pat. No. 2,800,307 issued July 23, 1957 to Putney for "Apparatus . . . ".

The refrigeration system for reactor 100 is a closed cycle one, wherein the heat exchanging medium is input to header 108 through line 113, taken off through line 114 and passed to compressor 115. Discharge from the compressor is into line 116, through condenser 117 and from the condenser through line 118 to accumulator vessel 119. Back pressure valve 119a is provided on line 113.

Isobutane is fed into the system through line 120 which joins main feed line 121 to reactor 101. Olefin is fed into the system through line 122, heat exchanged at 123 and input to the reactor through line 124. Alternatively, line 124 may join line 121.

In the reactor, isoparaffinic hydrocarbons are alkylated with olefinic hydrocarbons in the presence of an acid catalyst and the effluent alkylate, excess isoparaffinic hydrocarbons and acid are withdrawn from the vessel through line 125, passing to acid settler 126. Acid is withdrawn from settler 126 through line 127 with spent acid being removed from the system through line 128 and new acid being added to the system through line 129. Pump 130 passes recycle acid from settler 126 and new acid from line 129 into the vessel through line 131.

The hydrocarbon effluent from settler 126, including excess isoparaffinic hydrocarbons and alkylate, is passed through line 132 in heat exchange with the olefin feed at 123 to optional neutralization shown schematically at 133. From the neutralization step, line 134 passes the hydrocarbon effluent to heat exchanger 135 where heating medium to be described heats the net hydrocarbon effluent to drive off isoparaffinic hydrocarbons therefrom. Exchanger 135 is a vaporizing condenser.

The heated effluent is then passed through line 136 to effluent flash drum 137. The vapors evolved at the heat exchanger 135 are drawn off from the flash drum through line 138, passed to condenser 139 and from thence through line 140 to accumulator vessel 141. From accumulator 141, line 142, passing through pump 143, recycles the isobutane to main feed line 121 and from thence into reactor 100. Accumulator 141 and pump 143 may not be necessary in some installations as, in many cases, the operating pressure of the effluent flash drum will be high enough to force the condensate back to the reactor without requiring a pump.

The heated, vapor withdrawn hydrocarbon effluent is taken off the bottom of effluent flash drum through line 143. Neutralization may optionally be performed at 144, with the net hydrocarbon effluent in any case being passed to deisobutanizer tower 145. Reboiler 146 of conventional type, or several of such, may be provided on the deisobutanizer tower. Normal butane may be withdrawn from the tower through line 147. Normal butane, other paraffinic hydrocarbons and alkylate product are withdrawn from the system through line 148.

The overhead from the deisobutanizer tower, comprising isobutane and other light hydrocarbons, is passed through line 149 to compressor 150, where the vapors are compressed and heated to serve as a heat exchange medium at heat exchanger 135. Line 151 from the compressor discharge passes to heat exchanger 135 and thence passes to join main feed line 121 after optional condensation at 152. Alternatively, all or part of the isobutane rich vapors from tower 145 may be passed through line 153 (valve controls at 154 and 155) to condensation at 156 and thence into accumulator drum 157. Bottoms from drum 157 in line 158 are pumped (159) back to the tower in line 160 (valve controlled at 161) or all or partly back to the reaction via line 162 (valve controlled at 163).

The entire or major part of the heat exchanging medium for heating the net hydrocarbon phase effluent in line 134 may be provided from the closed cycle refrigeration system in the upper left hand corner of FIG. 2. Thus, line 164 (valve controlled at 165 as is line 116 at 166) preferably has booster compressor 167 thereon to further heat by compression some of the vapors from the closed cycle refrigeration system previously described. The said super-compressed vapors are passed to vaporizing condenser 168 on line 169 where they give up heat to the net effluent portion (none, some or all) passing through line 169. Valves 170 and 171 on lines 169 and 136 control the flow quantities therethrough. After at least partial cooling and condensation at exchanger 168, the said vapors are returned to line 116 before cooler/condenser 117.

The basic objective of the effluent pressure flash system in the FIG. 2 system, the FIG. 1 system and that to be described, is to provide a simple means of increasing the quantity of isobutane recycle in an alkylation system without requiring the expansion of the deisobutanizer tower and its accessory equipment. In the effluent flash vaporization system, the net hydrocarbon effluent from the reactor section, after heat exchange with the various feed streams, and optional neutralization, is heated under any desired pressure to a suitable temperature and the hot effluent is discharged into a separating drum.

When sufficient heat is applied to the effluent, the temperature thereof will be increased to its boiling point at the operating pressure and, if additional heat is applied, vapors will be formed. In passing through the transfer line between the heater and separating drum, an equilibrium is established between the liquid and the vapors and the latter may be withdrawn from the top of the separator. These vapors, in a normal alkylation system, will contain a high percent of isobutane. In the system shown, the vapors are condensed, typically by cooling water, and the condensate is recycled to the alkylation reactor. Liquid remaining after the effluent flash vaporization is charged to the deisobutanizer tower in the customary manner.

Comparing FIG. 1 with FIG. 2, the same objects and advantages discussed apply, with the exception that in the FIG. 2 system, no vapors are evolved in the reaction zone. The efficiency of the process is effected, however, by the isobutane concentration of the hydrocarbon liquid in contact with the catalyst. Again, using a given deisobutanizer with a given overhead recycle rate, the effluent flash system shown may be used to increase the equilibrium isobutane concentration throughout the reactor vessel materially.

FIG. 3 EFFLUENT REFRIGERATION

Figure 3:
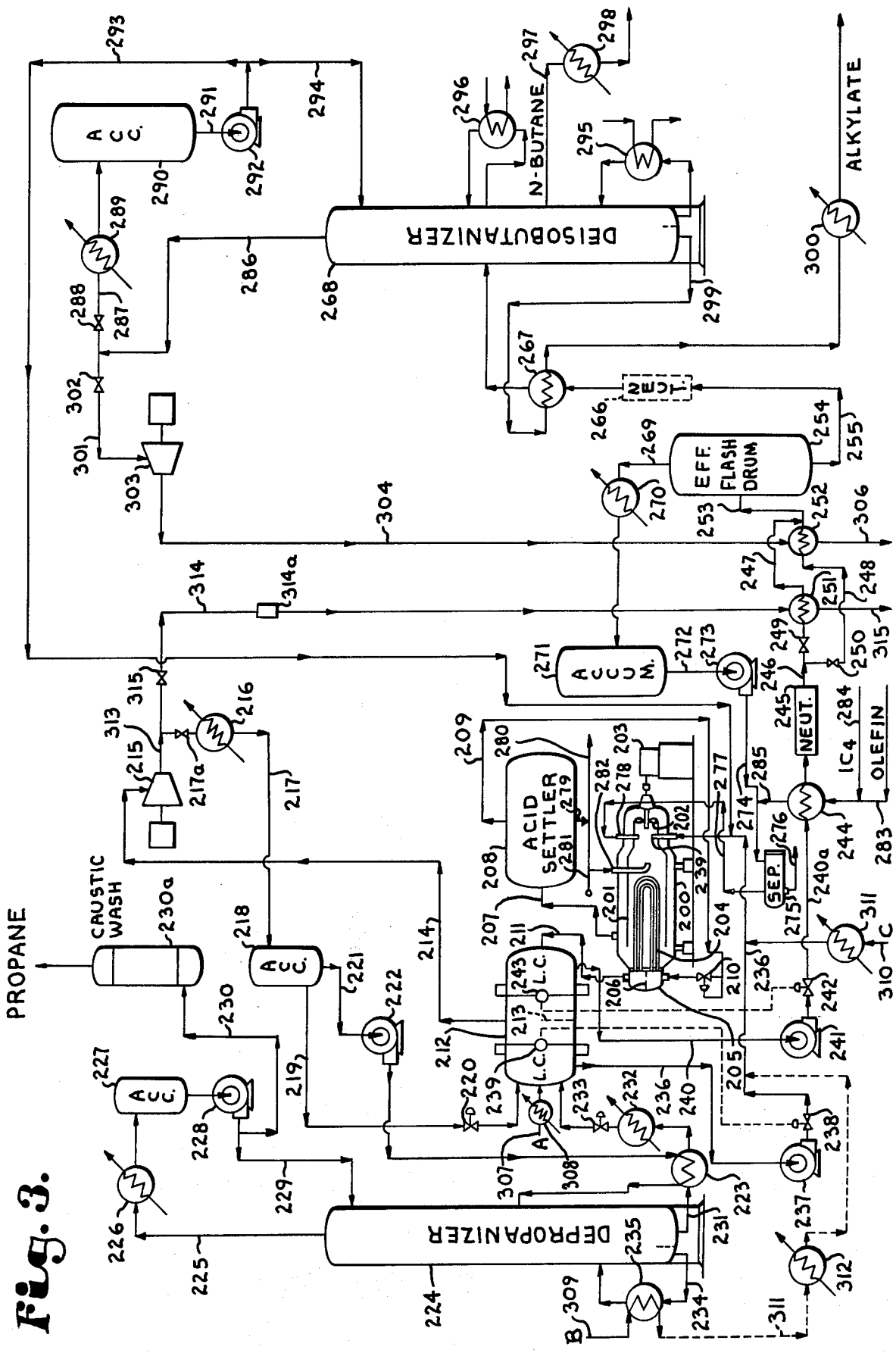
FIG. 3 is a schematic flow diagram of an alkylation system utilizing effluent refrigeration to cool the reaction step.

Referring to FIG. 3, therein is shown a sulphuric acid alkylation process, apparatus array and system wherein a circulating reaction vessel of the Stratco contactor type is employed with indirect heat exchange by effluent refrigeration of the reaction zone. With the exception of the effluent flash vaporization system and heating sources therefor, as well as the recycles therefrom, the combination of apparatus and flow line linkages is essentially conventional.

In this Figure, the numbering begins with 200 to avoid confusion with the previous Figures.

Contactor 200, here shown as horizontal, has a circulating tube 201 with an impeller 202 at one end thereof driven by a power source 203. Tube bundle 204 extends from the header 205 which is divided centrally by plate 206. In vessel 200, olefinic hydrocarbons are alkylated with isoparaffinic hydrocarbons in the presence of acid catalyst, typically here sulphuric acid catalyst, in conventional manner with reaction effluent, comprising alkylate, excess isoparaffinic hydrocarbons, polymeric acid contaminants and the like being taken off overhead through line 207 to acid settler 208. The hydrocarbon phase of the reaction effluent is taken off overhead from the settler via line 209 and passed to the input side of the tube bundle after back pressure valve 210. The latter maintains the reaction under liquid phase conditions and the cooling after expansion through such valve of the hydrocarbon phase of the reaction effluent, according to well established practice in effluent refrigeration, maintains the reaction zone temperature as desired.

From the upper portion of header 205, line 211 carries the hydrocarbon phase effluent, both liquid and vapor, to trap and flash drum 212. This vessel has a divider 213 centrally thereof which divides the liquids in the sides thereof but permits communication thereover for vapor phase from both sides of the trap and flash drum 62.

Vapor overheads from trap 212, comprising light excess isoparaffinic hydrocarbons and normal paraffinic hydrocarbons, are taken off through line 214, passing to compressor 215. One line 217 from the discharge of compressor 215 is valve controlled at 217a and has condenser 216 thereon, line 217 leading to accumulator vessel 218. Liquid from accumulator 218 may pass through line 219 through valve 220 back to trap and flash drum 212 or, alternatively, bottoms liquid is taken off through line 221 via pump 222 through a heat exchange at 223 to depropanizer tower 224.

The overhead from tower 224 is taken off through line 225, through cooler 226 and to accumulator 227. Bottoms from accumulator 227 may return to tower 224 through line 229 or go out of the system through line 230 with an optional caustic wash step at 230a. Pump 228 drives the bottom liquid from accumulator 227 through lines 229 and 230, which are valve controlled (not shown). Bottoms from depropanizer tower 224 are returned through line 231 through heat exchange 223 and through a cooling step at exchanger 232 and valve 233 to the bottoms of trap and flash drum 212. Reboiling takes place via line 234 with heat at 235 from sources to be described.

Liquid bottoms from the left hand side of trap and flash drum 212 are returned and handled with respect to the alkylation reaction and associated systems via line 236, pump 237 and valve 238 controlled by level control 239. Line 236 returns the trap bottoms, largely comprising unreacted isoparaffinic hydrocarbons, via input fitting 239, comprising a nozzle, to a position interior of the circulating tube before impeller 202.

On the right hand side of barrier 213 in the trap and drum 212, bottom liquids are returned to the system via line 240 through pump 241 and valve 242 controlled by level control 243. From valve 242, the trap bottoms are passed via line 240a through heat exchange at 244 to an optional neutralization step at 245. This neutralization step may be a conventional caustic wash and water wash step (wet) or a bauxite neutralization (dry).

From neutralization step 245, line 246 divides into lines 247 and 248 valve controlled at 249 and 250, respectively. The contents of line 247 are heat exchanged at 251 in a manner to be described, while the contents of line 248 are heat exchanged at 252 in a manner to be described. Lines 247 and 248 join in common line 253 which passes to effluent flash drum 254.

Bottoms from flash drum 254 are taken off through line 255, passing through optional relocated neutralization step (as previously described) at 266 and heat exchange at 267 to deisobutanizer tower 268. The overhead from effluent flash drum 254 is taken off through line 269, condensed at 270 and passed to accumulator vessel 271. Liquid from accumulator vessel 271 is taken off via line 272, driven by pump 273 (if required) and thence passed via line 274 to water separator 275. From the latter vessel, water is taken from the system via line 276, the output from the separator vessel through line 277 going to input fitting or nozzle 278 which feeds the contents of line 277 ahead of impeller 202 within circulating tube 201.

Referring back to settler 208, the acid recycle from settler 208 is via line 279 with spent acid going out of the system at 288 and new acid going into the system at 281, the acid recycled going into the contactor in the circulating tube through nozzle or fitting 282. Olefinic hydrocarbons are input to the system through line 283, this line joined by line 284 supplying new isoparaffinic hydrocarbons, the common line 285, after heat exchange at 244, joining line 274 before separator 275.

The overhead from the deisobutanizer tower 268 is taken off through line 286 and, via one line 287 valve controlled at 288 and condensed at 289, the light overhead from deisobutanizer tower 268 may be accumulated in vessel 290. Bottoms from accumulator 290 are taken off through line 291, this liquid driven by pump 292. Line 291 splits into recycle line 293 which passes back into the alkylation system to join line 236 after valve 238 and recycle line 294 back to deisobutanizer tower 268. Lines 293 and 294 are valve controlled (not shown).

Reboilers 295 and 296, for the upper and lower portions of tower 268, are conventionally supplied. Depending upon the conditions in tower 268, normal butane may be taken off the tower at 297 and cooled or condensed at 298 to be removed from the system. Liquid bottoms from the deisobutanizer, particularly including alkylate, are taken off through line 299 and passed in heat exchange with the contents of line 255 at 267 and thence out of the system after cooling or condensation at 300.

The heat exchange of the flash drum and suction trap bottoms in the effluent flash vaporization system will now be described. The light isoparaffinic hydrocarbon overhead through line 286 from deisobutanizer tower 268 can serve as one source of heat for this flash vaporization system. Line 301 is valve controlled at 302, with the contents thereof passing to compressor 303. Discharge line 304 from compressor 303, passes to exchanger 252 to heat the contents of line 248. Discharge line 306 from heat exchanger 252, (1) may be joined with line 307 (at A) which, after cooling and condensation at 308 enters flash drum and trap 212, (2) may join line B numbered 309 supplying to heat to the reboiler 235 on depropanizer 224 or, (3) joins line C numbered 310 which, after cooling or condensation at 311 joins line 236. Thus, light isoparaffinic hydrocarbons compressed for heating at compressor 303 heat the contents of line 248 and thence, after cooling and condensation are passed back into the alkylation system at A (307), B (309) or C (310). The output from reboiler 235 is carried by line 311 to condenser 312 which rejoins line 236 after valve 238. The return from line 306 may be split between A, B and/or C as desired or join line 315 to be described.

The other source of heat for the effluent flash vaporization system of FIG. 3 comes from the overhead vapors taken off through line 214 from trap and flash drum 212. The compressor discharge from compressor 215, discharged through line 313, may be passed, in whole or part, into line 314, valve controlled at 315. The compressed, heated isoparaffinic hydrocarbon vapors from line 214 are passed through line 314 to heat exchanger 251 and, thereafter, into line 315. Line 315 joins one or more of lines 306, 307, 309 or 310. That is, the condensed, or partly condensed isoparaffinic hydrocarbon vapors, after heat exchange at 251 may be joined with the partially or wholly condensed isoparaffinic hydrocarbon vapors in line 306 and passed to lines A, B or C, or any combination of them or, alternatively, separately passed to any one or several of lines A, B and C.

Booster compressor 314a is preferably employed on line 314 after valve 315 to further compress vapors in line 314 to the desired heat content before exchange at 251.

In the event that is desired only to use the vapors from line 214 as the heating source, line 248 is shut off. Likewise, if only vapors from line 286 from deisobutanizer 268 are to be used as the heating source for the flash vaporization system, line 247 is shut off. Generally speaking, both heating sources are preferably used and, in each case the substantial or entire portion of the vapors from either line 214 or 286, or both of them are employed.

As previously stated, in the effluent flash vaporization system, the net hydrocarbon effluent from the reactor section, after heat exchange with the various feed streams, and optional neutralization, is heated under any desired pressure to a suitable temperature and the hot effluent is discharged through line 253 to separating or flash drum 254. When sufficient heat is supplied to the effluent in exchangers 251 and/or 252 the temperature thereof will be increased to its boiling point at the operating pressure and, if additional heat is applied, the vapors are formed. In passing through the transfer line between heaters 251 and 252 and drum 254, an equilibrium is established between the liquid and the vapors and the vapors are withdrawn from drum 254 through line 269. These vapors, in a normal alkylation system, contain a high percentage of isobutane. They are condensed at 270 and the condensate is recycled to the alkylation reactor from accumulator 271. The liquid in flash drum 254 remaining after the vaporization is charged to deisobutanizer tower 268 through line 255. This effluent flash system increases the equilibrium isobutane concentration in the reactor materially.

FIG. 4 STRUCTURE AND FUNCTION

Figure 4:
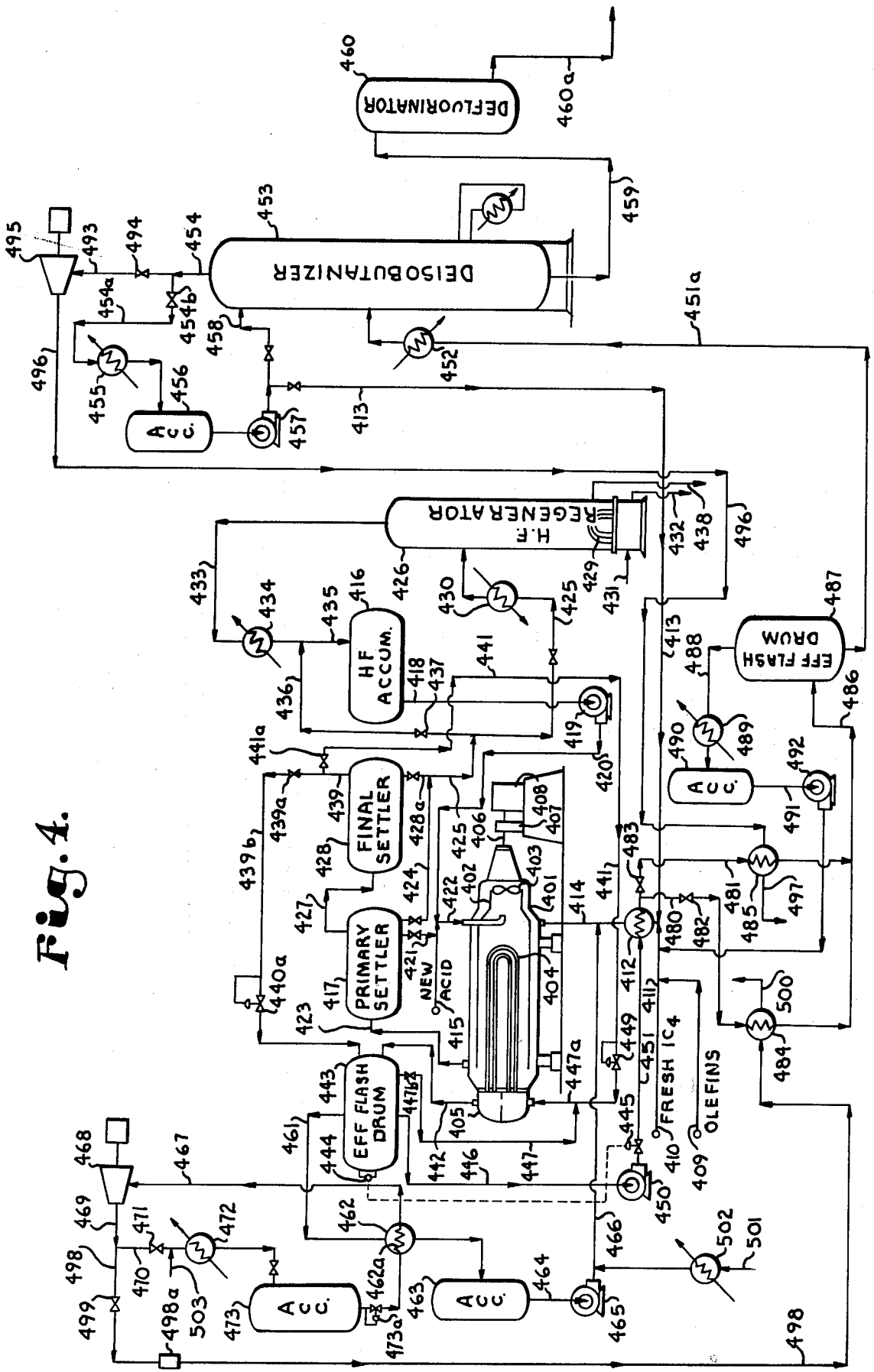
FIG. 4 is a schematic flow diagram of an alkylation system utilizing various forms of effluent refrigeration to cool the reaction step, the catalyst employed particularly being hydrogen fluoride.

Referring to FIG. 4, at 401 is seen the shell of a reactor equipped with an open ended circulating tube 402. At one end of the circulating tube is an impeller 403 which serves the purpose of a circulating pump in cooperation with the circulating tube. Within tube 402 are a plurality of heat exchanger elements 404 comprising a tube bundle provided with a distributing head 405 enclosing one end of the reactor. Impeller 403 is mounted on a shaft 406 rotated through a reduction gear 407 by any suitable source of power or prime mover such as an electrical motor or steam turbine seen at 408.

Circulation within the reactor is established by the impeller through the annular space between the shell 401 and circulating tube 402 around the cooling or heat exchange tubes 404 and back to the impeller. Olefinic hydrocarbons and isobutane in excess are introduced to the system through lines 409 and 410, respectively and are combined in feed pipe 411 prior to passage through heat exchanger 412. Recycled isobutane from fractionation may be returned through pipe 413 and introduced into the hydrocarbon mixture before reaching heat exchanger 412, constituting a portion of the feed supplied to the reactor through pipe 414.

Fresh acid is supplied to the system through line 415, being combined with recycle acid from accumulator 416 and acid bottoms from primary acid settler 417. The recycle acid is returned through line 418, pump 419 and line 420, while bottoms from primary settler 417 are returned to the reactor through 421. Fresh and recycle acid enter the reactor through pipe 422.

Hydrocarbons supplied through lines 409 and 410 combined with recycled isobutane are mixed in the reactor with the acid catalyst introduced through pipe 422. Alkylation of the isoparaffinic hydrocarbons by the olefinic hydrocarbons takes place in the reactor while the mixture is being rapidly circulated and agitated by impeller 403 which assures mixing of the hydrocarbons and acid catalyst. The reaction is strongly exothermic.

The effluent mixture of hydrocarbons and acid is discharged from the reactor through pipe 423, passing first to the primary acid settler 417 where it is permitted to separate into a hydrocarbon phase and an acid phase. The acid phase is withdrawn from the bottom and is either returned to the reactor through pipes 421 and 422 or diverted through pipes 424 and 425 to the acid regenerator 426. Valves are interposed in these lines to govern the amount of acid returned to the reactor and diverted to the regenerator.

The hydrocarbon phase separated in primary settler 417 is discharged from the top through pipe 427 into final acid settler 428. In the final settler, the effluent mixture of hydrocarbons separates from what undissolved, or "free", acid remains, typically approximately one percent by weight remaining in the hydrocarbon phase material, the acid bottoms being withdrawn through a discharge line 428a connected to the acid discharge pipe 425 through which the acid bottoms from the primary acid settler flow to acid regenerator 426. Acid bottoms from settlers 417 and 428 pass through lines 424 and 425 to regenerator 426 which is equiped with a heating coil 429. Preheater 430 is interposed in line 425 ahead of regenerator 426. Input and discharge fluid lines 431 and 432 serve to circulate a heat exchanging medium through coil 429 in the bottom of the acid regenerator 426.

Regenerated acid passes from the top of regenerator 426 through line 433 and, after condensation at 434, is delivered through pipe 435 into acid accumulator 416. Bypass flow line 436, controlled by valve 437, may be used to bypass regenerator 426 or divert a portion of the acid bottoms from settlers 417 and 428 to accumulator 416. As previously noted, acid from accumulator 416 is returned through lines 418 and 420 to the reactor. Sludge and tars are removed from the bottom of regenerator 426 through line 438 to suitable disposal.

The hydrocarbon phase effluent from the acid settling stage taken off through line 439 contains approximately 0.5 to 1.5 percent by weight of hydrocarbon fluoride, only a small portion of which is in solution with the balance free acid. If this material were passed directly to deisobutanizer 453, there would be a severe corrosion problem occassioned by the free acid at elevated temperature. Likewise, if a neutralization step were imposed between the acid settling stage and the deisobutanizer tower 453, there would be a severe neutralization problem. If an alloy stripper were interposed directly between the final acid settler and the deisobutanizer tower 453, there would be the expense of this equipment and, additionally, there would be no benefit derived in the way of effluent refrigeration from the hydrocarbon phase. The instant method contemplates three alternatives.

In the first alternative, the entire hydrocarbon phase effluent is passed through line 439b, pressure reduced at valve 440a and from thence passed at greatly increased velocity into effluent flash drum 443. Recycle of liquid through line 447, line 447a, distributing head 405, tube bundle 404 and line 442 is carried out until a flash vaporization equilibrium is reached in the vapor withdrawal step (at the existing temperatures and pressures) within flash drum 443 at which substantially all of the hydrogen fluoride carried in the hydrocarbon phase is vaporized. As the equilibrium constants of the hydrogen fluoride in the hydrocarbon phase effluent are quite different, this is feasible. Circulation of liquid through the tube bundle 404 in such case is effected by the gas lift effect of the vapors formed within the tubes. It is necessary that drum 443, lines 447 and 442 and tube bundle 404 be so sized and of such heat exchanging capacity relative a given reaction step that such flash vaporization equilibrium may be achieved.

The second modification of the process contemplates the passage of a portion of the total hydrocarbon phase effluent from acid settler 428 through line 439b to effluent flash drum 443 after pressure reduction at 440a. Sufficient total hydrocarbon phase effluent, both liquid and vapor without separation, is passed through line 439b, and, as well, second line 441 and its pressure reducing valve 449, distributing head 405, bundle 404 and line 442 to provide a flash vaporization equilibrium in the vapor withdrawal step at 443 at which at least substantially all hydrogen fluoride is vaporized. If an insufficient amount of hydrocarbon phase effluent is passed through line 439b to provide such equilibrium through tube bundle heat exchange, recycle of liquid from trap 443 through lines 447, 447a and 442 through tube bundle 404 and distributing head 405 may be required to achieve the critical flash vaporization equilibrium. Such liquid can be educted at the juncture of lines 447 and 447a by the high velocity flow in line 441. Thus, the stream of hydrocarbon flowing at high velocity after pressure reduction at valve 449 draws into pipe 447a liquid from flash drum 443 through pipe 447.

The third modification of the subject process contemplates the passage of the entire hydrocarbon phase effluent, including both liquid and vapor without separation, through line 441, back pressure valve 449 and line 447a into distributor head 405, tube bundle 404 and line 442 to effluent flash drum 443, whereby to achieve the critical flash vaporization equilibrium with substantially all the acid removed. It is contemplated that, in such case, any recycle through lines 447 and 442 will be only rarely required. If the equilibrium is not reached, however, such recycle may be employed, preferably with eduction at the juncture of lines 447 and 447a. The relative quantities of flow through lines 441 and 439b is controlled by valves 439a and 441a, respectively, on such lines. Valve 447b on line 447 controls recycle, if any, from flash drum 443.

Back pressure valves 440a and 449 are designed to hold sufficient back pressure on the reactor-settler system to prevent any evaporation of the hydrocarbon components contained therein. A liquid level control 444 manipulating valve 445 regulates discharge of liquid from flash drum 443 through pipe 446 driven by pump 450.

Although hydrofluoric acid alkylation is usually carried out in the range of 60 to 100 degrees F. in a system wherein a small amount of propane is also present and the reaction temperature is controlled at about 33 degrees F. to 55 degrees F., the back pressure maintained on the settler by valve 449 will be in the order of 40 psig to 100 psig. Upon passing pressure reduction valve 440a or 449, pressure upon the hydrocarbons passing into the cooling elements is reduced to the order of 0 psig to 10 psig, causing a considerable portion of the lighter components of the effluent to vaporize, resulting in the cooling of the entire hydrocarbon phase. Depending on the pressure established within the cooling elements of tube bundle 404 of the reactor, the temperature of the hydrocarbon effluent phase will be reduced to a figure normally within the range of 15 degrees F. to 30 degrees F. by evaporative cooling, making it suitable for use as the cooling medium for the reaction.

The liquid withdrawn from the effluent flash drum 443 through pipe 446 is returned by pump 450 and pipe 451 to heat exchanger 412 where it is brought into heat exchange relationship with the incoming feed stock supplied through pipe 414. From heat exchanger 412, the liquid passes through an effluent flash vaporization system which will be described hereafter. From the flash vaporization system, light hydrocarbon relieved hydrocarbon phase effluent passes through line 451a and preheater 452 to deisobutanizer 453 where the light fraction hydrocarbons rich in isobutane are taken off overhead through pipe 454 and optionally condensed at 455 with the condensate being collected in receiver 456. Condensate accumulated in vessel 456 may be either returned to tower 453 by pump 457 in pipe 458 or returned in whole or part by pump 457 and line 413 as isobutane recycle. Alkylate product is recovered from the bottom of tower 453, same passing off through line 459 to defluorinator 460, thence to debutanizer and rerun towers, not shown, through line 460a.

Vapors separated from the hydrocarbon effluent in flash drum 443 are taken through line 461 to condenser 462, after which the condensate is collected in vessel 463. Bottoms from accumulator 463 are recycled to feed pipe 414 through line 464, driven by pump 465 into line 466. Effluent flash drum 443 is typically operated at a pressure in the order of 15 to 25 psia when the reactor is held at 50 degrees F. Vapors leaving flash drum 443 pass to condenser 462 and accumulator 463 which are operated at approximately the same pressure.

The cooling medium at condenser 462 is provided by a closed cycle refrigeration system such as, for example, one utilizing freon 12 or propane. This refrigeration system includes heat transfer coil 462a in condenser 462, connected to compressor 468 by line 467, with discharge line 469 from compressor 468 splitting into two lines. One of them, line 470, valve controlled at 471, passes through condenser 472 to accumulator 473. This refrigeration system is operated to provide a condensing temperature in the order of 15 degrees F. It is operated as a closed cycle so that none of the refrigerant comes in contact with the hydrocarbons being processed or the hydrogen fluoride catalyst. Even more important, none of the hydrogen fluoride comes in contact with the compressor. Back pressure valve 473a is positioned on line 467 between accumulator 473 and condenser 462.

By means of this refrigeration system, effluent vapors withdrawn from flash drum 443 are condensed and their temperature is reduced commensurate with the temperatures of the circulating refrigerant. Under normal operating conditions, condensate collected in accumulator 463 will have a temperature of approximately 15 degrees to 25 degrees F. The quantity of isobutane in this condensate stream recycled through pipe 466 will normally be in the order of 4 to 7 parts by volume for each part of olefin in the fresh feed.

Turning to the effluent flash vaporization system, as has been previously described, the bottoms from the effluent flash drum are passed through line 446, via pump 450 and control valve 445 into line 451 to heat exchange at 412. Line 451 exiting from exchanger 412 splits into lines 480 and 481 valve controlled at 482 and 483, respectively. The net hydrocarbon phase effluent which is coming off the bottoms of effluent flash drum 443 may thus be divided in any ratio preferred (all, any part or none) in either line. Hydrocarbon phase effluent in line 480, controlled by valve 482, passes to heat exchange at 484, while that portion of the hydrocarbon phase effluent in line 481 passes to heat exchange at 485. After heat exchange at 484 and 485, lines 480 and 481 join in a common line 486 passing to effluent flash drum 487. Heat is supplied at exchangers 484 and 485 to the net hydrocarbon phase effluent in lines 480 and 481 (or either of them) in such manner as to drive off a substantial proportion of the light hydrocarbons, particularly including isobutane, therefrom in the manner described with respect to the previous figures.

Bottoms from effluent flash drum 487, comprising the net hydrocarbon phase effluent less a considerable quantity of the lighter hydrocarbons, particularly isoparaffinic, pass through line 451a to deisobutanizer 453. Overhead from flash drum 487 goes via line 488 to condensation at 489 and accumulation at 490. The accumulated light hydrocarbon liquid is taken off accumulator 490 via line 491, driven by pump 492 and passed directly into the common feed line 411.

The heat source for the flash vaporization system heat exchangers at 484 and 485 may be supplied from one or both of two sources. The first of these involves overhead light hydrocarbon vapors from the deisobutanizer, particularly isobutane, through line 454. Line 454 is divided into line 454a, valve controlled at 454b and line 493, valve controlled at 494. All or part of the overhead from deisobutanizer 453 may be passed into line 454a. In the former case valve 494 is closed. Alternatively, all or part of the overhead from deisobutanizer 453 may be passed into line 493, in which case valve 454b is entirely or partly closed and valve 494 entirely or partly open. At any rate, the light hydrocarbon vapors from line 454 passing into line 493 through valve 494 go to compressor 495. The discharge line 496 from compressor 495, containing hot, compressed light hydrocarbon vapors, mostly isobutane, goes to heat exchanger 485, exiting therefrom as line 497.

The other source of heat for flash vaporization at 484 and 485 comes from the hot, compressed vapors from compressor 468. In such case, line 469 divides into line 470, previously mentioned, valve controlled at 471 and line 498, valve controlled at 499. A greater or lesser portion, as determined by valves 471 and 499, of the hot compressed gases from discharge line 469 of compressor 468 are taken through line 498 to heat exchange at 484 with the discharge line therefrom being line 500. A booster compressor, schematically seen at 498a, may be employed to further compress and heat vapors in line 498 before heat exchange at condenser 484.

Assuming heat is supplied at exchanger 485 from line 496, the discharge line 497, containing partly or wholly condensed light hydrocarbon vapors, mostly isoparaffinic or isobutane, may be joined into line 501 with further condensation or cooling at 502. Line 501 then passes into line 466 joining feed line 414 after heat exchange at 412. The heat used (if any) at vaporizer-condenser 484 is taken from hot, compressed vapors of freon, propane, ammonia or the like from the closed cycle refrigeration system associated with condenser 462. After passage of these vapors through the latter, and heat exchange, they are returned to the closed cycle system via line 503 between valve 471 and condenser 472 on line 470.

FIG. 5

Figure 5:
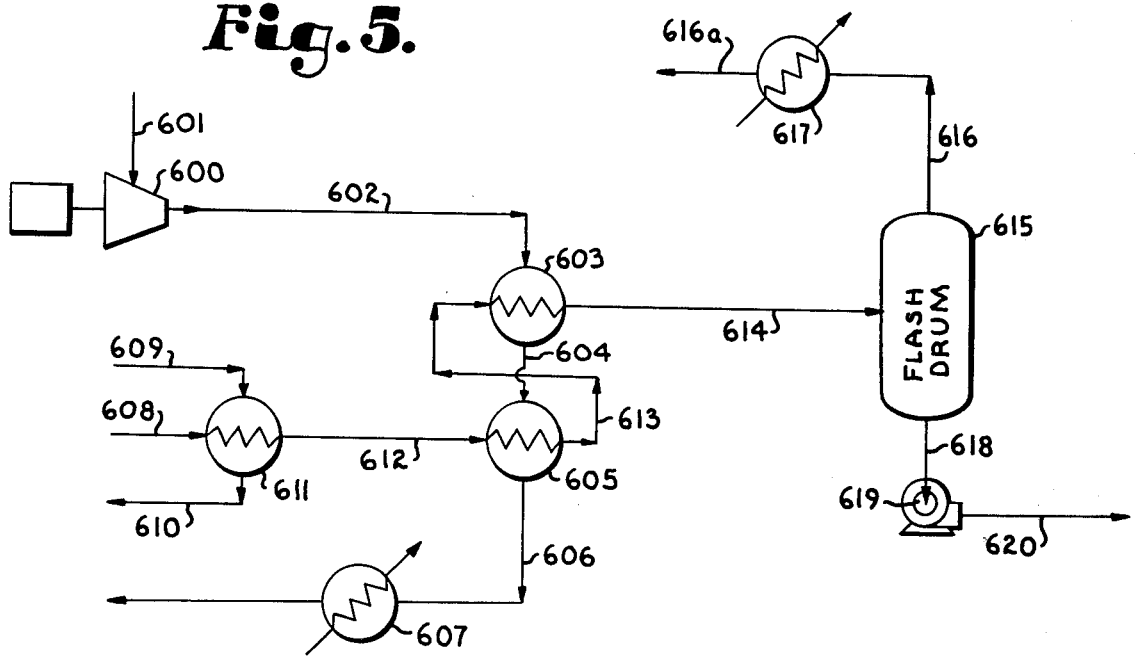
FIG. 5 is a fragmentary schematic flow diagram of an alternative flash vaporization heating system utilizing vaporizing condensers arranged in series.

The showing of FIG. 5 illustrates the use of two vaporizer-condensers in series utilizing the hot, compressed gases from a given compressor to heat exchange the net hydrocarbon effluent in the flash vaporization step. This system (two vaporizer-condensers in series) could be substituted for any one of the vaporizer-condensers in the systems illustrated, for example, condensers 54 and 56 in FIG. 1, 135 and 168 in FIG. 2, 251 and 252 in FIG. 3 and 484 and 485 in FIG. 4. Said otherwise, wherever a single vaporizer-condenser is shown in one of the figures, the double condenser system of FIG. 5 could be employed. If the system of FIG. 5 were substituted for each vaporizer-condenser shown in the figures, each figure would show four condensers. Compressor 600 may substitute for any compressor used as a hot compressed gas source for flash vaporization heat exchange in any of the previous Figures.

Referring to the drawing, a compressor 600 is fed by line 601 with vapors to be compressed, thus heated therein. The compressor discharge is into line 602 leading to first vaporizer-condenser 603. From first condenser 603, line 604 passes condensate and gases after a first heat exchange to second vaporizer-condenser 605. Discharge from vaporizer-condenser 605 is into line 606. If the vapors input into compressor 600 through line 601 are largely isoparaffinic hydrocarbons or isobutane, then line 606 leads back to the reactor (not seen), typically after condensate cooling step 607.

For example, in such case, line 606 would be equivalent to either line 88 or 89 of FIG. 1, line 151 of FIG. 2, either line 306 or 315 of FIG. 3 or line 497 of FIG. 4.

On the other hand, if compressor 600 is fed by line 601 with closed cycle refrigerant vapors such as freon, propane, ammonia or the like, then line 606 typically would return to the closed cycle refrigeration system (and typically without cooling at 607) as is the case in line 164a of FIG. 2 and lines 500 and 503 of FIG. 4.

The heat exchange in the flash vaporization step is made with the net hydrocarbon effluent. Such is input to the system of FIG. 5 through line 608 with heat exchange by the olefin and isobutane feeds in lines 609 and 610 at heat exchanger 611. This liquid effluent exits from exchanger 611 in line 612, then passes through vaporizer-condenser 605. It exits therefrom in line 613, then passing through vaporizer-condenser 603. Exit line 614 passes to flash drum 615, carrying liquid and vapor, the latter having been generated in condensers 603 and 605. In flash drum 615, the vapor-liquid separation takes place with light hydrocarbon vapors, mostly isobutane, going off overhead through line 616 with condensation at 617. Bottoms from flash drum 615 are taken off through line 618, pump 619 passing such liquid hydrocarbons through line 620 to the deisobutanizer (not shown). Line 616a after condenser 617 passes the condensed light hydrocarbons overhead from flash drum 615 to an accumulator (not shown) and from there the hydrocarbons return to the reactor vessel.

As illustrated, the net liquid hydrocarbon effluent is first heat exchanged with the largely condensed vapors from compressor 600 in second condenser 605 with the already heat exchanged effluent then exchanged by the compressed gases in condenser 603. This provides the most efficient use of the heat in the gases from the compressor 600 in vaporizing light hydrocarbons from the net hydrocarbon effluent in the two vaporizing condensers 603 and 605 (or vaporizing condenser 603 and cooler 605 if the heat exchanging medium in vessel 605 is entirely or essentially condensate).

Flash drum 615 is equivalent to flash drum 55 in FIG. 1, flash drum 137 of FIG. 2, flash drum 254 of FIG. 3 and flash drum 487 of FIG. 4. The two vaporizer-condensers of FIG. 5 would substitute for any single vaporizer-condenser of the first four figures if staged flash vaporization of the net liquid hydrocarbon effluent or a portion thereof is desired by use of the hot compressed gases from compressor 600.

FIG. 6

Figure 6:
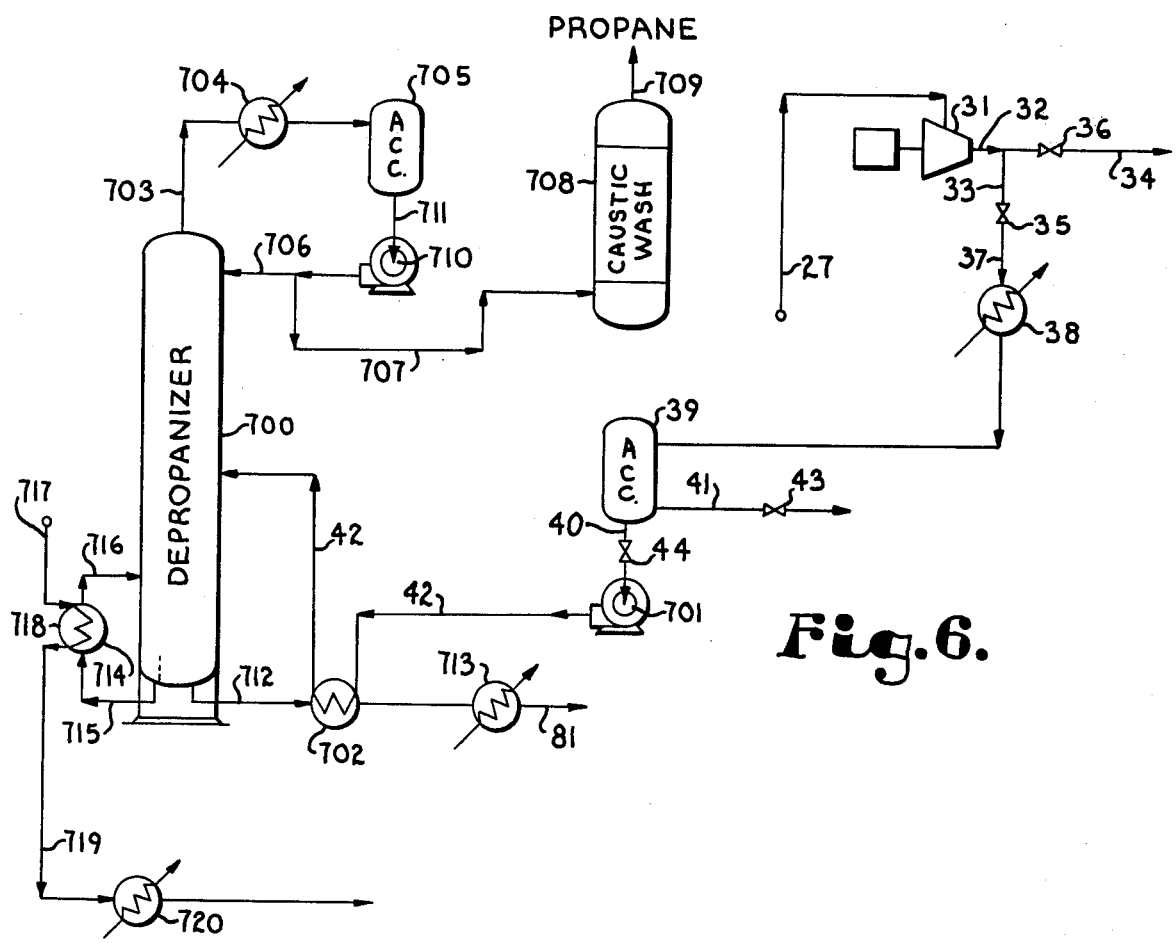
FIG. 6 is a fragmentary schematic flow diagram of a depropanizer unit shown as it would be connected into the system of FIG. 1.

FIG. 6 illustrates the use of some of the hot, compressed gases from one of the vaporizer-condensers 54 or 56 in FIG. 1 in heat exchange of a depropanizer associated with the alkylation reactor of that system. It also illustrates, in a portion of that figure, as will be described, how hot compressed gases from any one of the vaporizer-condensers of any of the figures may be used to heat exchange a depropanizer for most efficient use of the available heat in question before recycle of the gases with respect to some part of the alkylation reaction system.

Referring, then, to FIG. 6, parts of the system common to the alkylation reaction system of FIG. 1 are numbered the same and will briefly be redescribed here. Thus, light hydrocarbon overhead through line 27 passes to compressor 31. Discharge from compressor 31 into line 32 divides between lines 33 and 34 controlled by valves 35 and 36. The hot compressed gases in line 37 are condensed at 38 and passed to accumulator 39. Most of these hydrocarbons are recycled to the reactor through line 41 controlled by valve 43. A slip stream, however, is passed through line 42 valve controlled at 44 to depropanizer 700. This stream is pumped at 701 and heat exchanged at 702. The overhead from the depropanizer is taken off through line 703, through condenser 704 and to accumulator 705. Bottoms from accumulator 705 may return to tower 700 through line 706 or go out of the system through 707 with an optional caustic wash at 708. The propane line out of the system is 709. Pump 710 drives this last described system fed by bottom line 711 from the accumulator 705. The bottoms from depropanizer tower 700 are returned through line 712, heat exchange at 702 and a cooling step at 713 into line 81 to the reactor 10 in FIG. 1 as seen in that view.

Reboiler 714 is provided on depropanizer tower 700 with input line 715 thereto and output line 716 therefrom back to the depropanizer. Line 717 carries the heat source to coil 718 in reboiler 714 with output line 719 leading therefrom and optionally having cooler/condenser 720 thereon.

With respect to the system of FIG. 1, the feed to line 717 would come from either line 88 or 89 or (possibly, but not probably) both of them. In each case, in FIG. 1, the heat exchanging medium at the vaporizing-condensers 54 and 56 is hot, compressed light hydrocarbon vapors, particularly including isobutane. These vapors, after heat exchange and some condensation in condensers 54 and/or 56 are used as a heating medium in reboiler 714 typically as condensate. The output in line 719 is passed to the reactor 10. This can be a separate line with a separate condenser, as shown, or, alternatively, line 719 can connect with line 83 and cooler 90 serve the purpose of cooler/condenser 720.

In the event that a depropanizer is employed with respect to the system of FIG. 2, the light hydrocarbon vapors overheat from deisobutanizer 145, after compression at 150 and heat exchange in vaporizer-condenser 135, could be employed to heat exchange the reboiler of a depropanizer (not shown). In such case, lines 719 and condenser 720 in FIG. 6 are equivalent to line 151 and cooler 152 with liquid returned to the reactor through line 121 in FIG. 2.

In the system of FIG. 2, in the event that it is desired to use hot compressed gases from the closed cycle refrigeration system and compressor 115 and booster compressor 167, after a first heat exchange at vaporizer-condenser 168, to heat a depropanizer reboiler, the gases in line 164a are merely led through the reboiler before return to line 116 before condenser 117.

With respect to FIG. 4, the light hydrocarbon vapors from compressor 495 in line 496 are used for heat exchange in vaporizer-condenser 485. These partially condensed vapors could be used in heat exchange of a depropanizer reboiler before return to the reaction step via line 501. Alternatively, hot compressed vapors from compressor 468 and booster compressor 498a, after use as a heat exchange medium at vaporizer-condenser 484, may be taken via line 500 to a depropanizer reboiler before return to the closed cycle refrigeration system via line 503.

CONCLUSIONS

As has been previously described, I have provided three sources of hot, compressed vapors for indirect heat exchange with the net liquid hydrocarbon effluent in a flash vaporization separating step. This particularly include:

(1) Isobutane rich vapors produced by the heat of reaction in alkylation, either in the direct or indirect heat exchanging thereof. Thus, in FIG. 1, the isobutane rich vapors which are produced by the heat of reaction in direct heat exchange thereof are taken off vessel 10 through line 27 to compressor 31. In FIG. 3, isobutane rich vapors produced from the indirect heat exchanging of the alkylation reaction in vessel 200 are taken off suction trap 212 by line 214 to compressor 215. In each of these cases, the compressed, heated, isobutane rich vapors, with or without a booster compression step (34a in FIG. 1 and 314a in FIG. 3) may be used as all or part of the heat source in the flash vaporization separating step by indirect heat exchange with the net hydrocarbon phase effluent in a vaporizer-condenser.

(2) Light hydrocarbon vapors produced overhead from deisobutanizers which are produced by the heat of vaporization. Such have been shown alternatively as the sole or supplemental heat source in the flash vaporization separating step in each of the figures. In FIG. 1, overhead volatile vapors through lines 69 and 71 go to compressor 86. In FIG. 2, vapors through lines 149 and 149a go to compressor 150. In FIG. 3, vapors through lines 286 and 301 go to compressor 303. In FIG. 4, vapors through lines 454 and 493 go to compressor 495.

(It should be noted that, wherever isobutane rich vapors are employed as a heat exchanging medium in the flash vaporization separating step, such are, invariably, after use as a heat exchanging medium, fully condensed and returned to the reaction step to maintain the desired great excess of isobutane there.)

(3) Refrigerant vapors from a closed cycle refrigeration system which is associated with the alkylation system for one purpose or another. Such vapors may be freon, propane, ammonia or like volatile substances. The first example of a closed cycle refrigeration system associated with an alkylation system is seen in FIG. 2 where the entire reaction step in vessel 100 is indirectly heat exchanged with the closed cycle refrigeration system. Vapors therefrom, with an optional booster compressing step at 167, are usable as a heat exchanging medium in a vaporizer-condenser, returning to the closed cycle system before condenser 117. The second example is seen in FIG. 4, an alkylation system catalyzed with hydrogen flouride, where a closed cycle refrigeration system is used to condense the volatile hydrocarbon overhead from flash drum 443. Again, the refrigerant vapors, with an optional booster compression step, may be used as an heat exchange medium and then are returned to the closed cycle system before the condenser and after the compressor.

In short, the source of heat which is applied to the net hydrocarbon phase effluent in the flash vaporization separating step comprises volatile vapors which are normally present in quantity in at least one stage of the alkylation reaction system. These vapors either have been or are sufficiently heated by compression thereof to be at a temperature substantially above the temperature of the net liquid hydrocarbon phase effluent to be flash vaporized when it reaches the flash vaporization separating system. This source of heat may be volatile vapors normally present in separate stages of the alkylation reaction system (each drawing figure shows two such separate sources optionally usable).

The said hot, compressed vapors are separated from the alkylation reaction system stage in which they are normally present and passed in indirect heat exchanging relationship with the net liquid hydrocarbon effluent in a flash vaporization separating step in a vaporizing condenser. Thus, in the vaporizing condenser, at least a portion of the said hot, compressed vapors are condensed, while some of the lighter hydrocarbons in the net hydrocarbon phase effluent are vaporized therefrom. After use as a heat exchanging medium in the flash vaporization heating system, the said compressed, heated, heat exchanged and condensed vapors are then recycled to the alkylation reaction system for further use therein. Thus, as previously noted, the vapors from the closed cycle refrigeration systems are returned to such. The light hydrocarbon vapors from the deisobutanizer overheads are returned to the reaction step. Likewise, the light hydrocarbon vapors derived from the direct or indirect heat exchanging of the reaction step are returned to the reaction step. Optionally, a second heating step may be employed as seen in FIG. 6 at the depropanizer reboiler using the condensate from the vaporizer condensers.

It perhaps should be mentioned that, in the conventional use of compressors other than at the deisobutanizers of the various figures (31 in FIG. 1, 115 in FIG. 2, 215 in FIG. 3 and 468 in FIG. 4), the refrigerating vapors involved (FIGS. 2 and 4) or isoparaffinic rich hydrocarbons (FIGS. 1 and 3) are only compressed to the pressure that they can be condensed with cooling water in indirect heat exchange (38 in FIG. 1, 117 in FIG. 2, 216 in FIG. 3 and 472 in FIG. 4). In such case, the maximum water temperatures to be used in such cooling water condensation sets the pressure required of the condenser. On the other hand, in the present system, referring to the compressors in the left hand sides of the figures (non-deisobutanizer condensers), the refrigerant vapors or isoparaffinic hydrocarbons are being compressed to a further elevated pressure and permitted to at least partially condense in a hydrocarbon effluent vaporizer-condenser using boiling effluent hydrocarbons as a cooling medium. Such elevated pressure produces a concomitant elevated equilibrium temperature.

The hydrocarbons compressed in the deisobutanizer compressors 86 (FIG. 1), 150 (FIG. 2), 303 (FIG. 3), and 494 (FIG. 4) are likewise compressed to a relatively elevated pressure for the heat exchanging service in question. It is, of course, possible to use multi stage compressors with takeoffs of compressed vapors from different sections thereof in the place of the two separate compressors seen in the left hand side of the four figures.

EXAMPLE 1

As a first specific example of a flash vaporization system heat transfer utilizing the double vaporizer-condenser arrangement of FIG. 5, the following figures may be given. The immediate discharge from compressor 600 into line 602 comprises 118,953 pounds per hour of hot compressed gas at 194.7 psia and 192 degrees F. At the inlet to vaporizer-condenser 603, the pressure is 193.2 psia and 192 degrees F. Leaving exchanger 603 in line 604, the hot, compressed gases (condensed to a greater or lesser degree) are 188.9 psia at 155 degrees F. Leaving vaporizer-condenser 605 in line 606, the condensate is at 125 degrees F. and 183.9 psia. Assuming cooling water into cooler 607 at 90 degrees F. leaving at 105 degrees F., the condensate in line 606 after cooler 607 would be 100 degrees F. at 178.9 psia.

The liquid hydrocarbon feed being flash vaporized in vaporizer-condensers 605 and 603 would be at a temperature of 100 degrees F. entering condenser 605 in line 612 and at an ultimate temperature of 135 degrees F. in flash drum 615. The total condensation and some cooling of the gases in lines 602 and 604 takes place in vessels 603 and 605. Exchanger 607 employs cooling water for subcooling purposes.

The specific composition of the gases in this specific example present in line 602 comprises C-3 18,447 pounds/hour, IC-4 88,393 pounds/hour, NC-4 11,362 pounds/hour, IC-5 588 pounds/hour, NC-5 1 pound/hour and C6+ compounds 162 pounds/hour.

EXAMPLE 2

Another system utilizing a single vaporizer-condenser (as seen in FIG. 3 at 251) could employ 184 degrees F. temperature hot compressed vapors at 194 psia entering the condenser-vaporizer 251, exiting therefrom at 155 degrees F. and 191 psia. At the cooling water cooler (which would be on line 315 in FIG. 3, for example cooler 308 or 311) with water in at 90 degrees F. and out at 110 degrees F., condensate would exit at 100 degrees F. and 160 psia. The hydrocarbon phase effluent liquid passed to vaporizer-condenser 251 for vaporizing therein would enter at 100 degrees F. after feed heat exchange and pass to effluent flash drum 254 where the temperature would be 135 degrees F. at 105 psia pressure. After condensing overhead with cooling water, the light hydrocarbon recycle (from the effluent flash drum) would be in the range of 100 degrees F.

temperature and 95 psia pressure. Thus, the vapors into the vaporizing condenser(s) must be compressed to a temperature and pressure at which they can be condensed against the vaporizing net hydrocarbon phase liquid effluent. The latter statement applies to all cases. The specific example given employed the same composition of hot compressed gases as given in the previous example.

SYSTEM DESIGN

The calculations with respect to the vaporizing condenser heat exchangers and the effluent flash vaporization system are accomplished as follows with respect to the flash vaporization system of FIG. 3:

(1) For a given temperature past cooler 270 in line 269;

(2) For a given composition analysis of the effluent flash drum 254 bottoms discharge in line 255 to the deisobutanizer;

(3) For a given temperature of hydrocarbon phase net liquid effluent in line 246 past exchanger 244 and neutralization 245;

(4) Assuming a specific flow quantity recycle in line 272 from accumulator 271;

Then one may calculate:

(1) The vapor composition in line 269 leaving flash drum 254 and the pressure in drum 254;

(2) The pressure in accumulator 271;

(3) The duty on condenser 270;

(4) Using the analysis of compressor gases and a design allowance for minimum temperature differential in condensers 251 and 252, the vaporizing condenser outlet temperatures;

(5) After allowing a design pressure drop in vaporizing condensers 251 and 252 and piping to the compressors 215 and 303, the required compressor discharge pressures; and (6) Calculation of heat of compression gives the compressor discharge temperature.

COMPARATIVE ECONOMIES

The addition of a reactor section involving two Stratford/Graham contactors (for example, see Putney et al U.S. Pat. No. 3,759,318, issued Sept. 18, 1973 for "Contactor Improvements", also see FIG. 3 reactor 200) utilizing effluent refrigeration as seen in FIG. 3 to an already existing system utilizing an autorefrigerated reactor of the type seen in FIG. 1 was analyzed from the standpoint of utilizing effluent flash vaporization as disclosed in this specification in order that no change would be required in the existing deisobutanizer-debutanizer fractionation system.

Three options were considered:

(1) Using low pressure steam alone to flash the combined net hydrocarbon phase effluent from both reactor sections in a vaporizer-condenser prior to passage of same to fractionation after the effluent flash drum; (per U.S. Pat. No. Webb 3,055,958)

(2) Using a combination of hot, compressed gases from the suction trap of the Stratford/Graham reactor section plus low pressure steam for the heat sources to two flash vaporization system vaporizer condensers (the former analogous to line 214 to compressor 215 to condenser 251 in FIG. 3) and (3) Using only the hot, compressed isobutane rich gases from the reactor refrigerations of both the autorefrigerated and Stratford/Graham reactors as the heat sources to the flash vaporization system vaporizer-condensers (see FIG. 1 line 27, compressor 31, line 34 and condenser 56 and the aforementioned FIG. 3 line 214, compressor 215, line 314 and condenser 251). Thus, in this case, 100 percent of the effluent flash vaporization duty was provided by condensing refrigerant, while in case two only a part of such duty was provided by such, while in case one (equivalent to the Webb 3,055,958 patent aforementioned) none of the duty was so provided.

In this system, for the additional utilities required (over the existing plant rates, which include a C4 splitter with auxiliary equipment in all cases), the following utility quantity requirements were determined for the three cases specified:

(a) 20 psig steam in pounds/hour: (1) 40,679, (2) 22,171 and (3) and 11,583;

(b) cooling water in gallons per minute: (1) 6830, (2) 4661 and (3) 1226;

(c) driver horse power BHP (driver power converted to kilowatts): (1) 3071, (2) 3711 and (3) 4199.

The incremental utility costs per year (assuming $2.00/1,000 pound steam, 0.003/kwh and $0.04 M gallons) were, respectively, for the three systems noted, (1) $1,102,000, (2) $1,031,000 and (3) $950,000.

In short, the instant and subject described and disclosed flash vaporization system, where 100 percent of the effluent flash duty is provided by condensing refrigerant, as opposed to the Webb 3,055,958 patent system, where 100 percent of the duty is provided by steam, provides a saving in utilities of over $150,000 per year, or approximately 15 percent. It is thus demonstrated that the instant process involves substantial energy savings over Webb U.S. Pat. No. 3,055,958 as well as embodying all the advantages of Webb 958 with respect to basic equipment cost savings. In addition, no additional boiler capacity for steam was required in the subject system, only the provision of the additional compressor power.

ADDITIONAL VAPOR SOURCES

Previously, I have described the three sources of hot, compressed vapors for indirect heat exchange with the net liquid hydrocarbon phase effluent in a flash vaporization separating step. Alternative examples or sources of light hydrocarbon vapors available in typical alkylation reaction systems which may be compressed sufficiently for use in alkylation flash vaporization systems include the vapor overheads of depropanizers (thus line 225 from depropanizer 224 in FIG. 3 and line 703 from depropanizers 700 in FIG. 6) and debutanizers (not shown in any of the figures, but typically downstream from the deisobutanizers). These light hydrocarbon vapor streams, largely consisting of propane from depropanizers and normal butane from debutanizers, are the full equivalent of refrigerant vapors from closed cycle refrigeration systems which are associated with an alkylation system for one reason or another. The reason they are not equivalent to the light hydrocarbon vapors overhead from deisobutanizers or from the refrigeration of alkylation reactors (as seen in FIGS. 1 and 3) lies in the fact that such vapors, after compression and use as a heat exchanging medium, would not be returned to the reaction step, rather to the off lines from the system from whence they were drawn.

The only requirement in such case is sufficient compression of the depropanizer or debutanizer vapor overheads to provide the required minimum temperature difference for hydrocarbon phase effluent liquid evaporation and condensation of the said hot compressed vapors at the vaporizing condensers of the systems seen in the drawings, as well as sufficient quantity available to have a substantial effect in vaporizing the light hydrocarbons out of the net liquid hydrocarbon phase effluent stream. These condensate streams, after their duty in the vaporizer-condensers would be cooled and returned to the streams of such liquids (propane or butane) leaving the system.

As is well established in the art, the greater the temperature difference between the net liquid hydrocarbon phase effluent being vaporized and the hot compressed gases being condensed in the vaporizer-condensers, the less heat transfer surface is required in the vaporizer-condensers and vice versa.

From the foregoing, it will be seen that this invention is one well adapted to attain all of the ends and objects hereinabove set forth together with other advantages which are obvious and which are inherent to the process.

It will be understood that certain process features, steps and sub-combinations thereof are of utility and may be employed without reference to other features, steps and process subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

I claim:

1. A process of alkylating isoparaffinic hydrocarbons with olefinic hydrocarbons in the presence of an acid catalyst comprising the steps of:
    (1) Contacting isoparaffinic hydrocarbons with olefinic hydrocarbons in a reaction vessel in a reaction step in the presence of the acid catalyst and a large excess of isoparaffinic hydrocarbons,
    (2) Withdrawing catalyst, excess isoparaffinic hydrocarbons and alkylate product from the reaction vessel and step,
    (3) Passing alkylate product hydrocarbons and some excess isoparaffinic hydrocarbons, after their substantial separation from the catalyst as a hydrocarbon phase, to an indirect heating step utilizing at least one evaporative condenser, wherein sufficient heat is applied thereto to evolve a substantial proportion of said isoparaffinic hydrocarbons therein in vapor form therefrom,
    (4) Passing the said heated liquid hydrocarbon phase from said indirect heating step to a flash separating step where said isoparaffinic hydrocarbons are separated overhead therefrom,
    (5) Passing liquid bottoms from the flash separating step to a fractionation step where additional heat is applied thereto to evolve further isoparaffinic hydrocarbons in liquid form therefrom,
    (6) Condensing the overhead isoparaffinic hydrocarbon vapors from the flash separzation step and returning same in liquid form to the reaction vessel and reaction step for the purpose of maintaining the large excess of isoparaffinic hydrocarbons therein,
    (7) Further recycling some of the isoparaffinic hydrocarbon vapors from the fractionation step to the reaction vessel and step in liquid form for the same purpose,
    (8) Compressing volatile vapors normally present in at least one stage of the alkylation reaction system to a temperature substantially above the temperature of the hydrocarbon phase of step (3) before said hydrocarbon phase is heated in the heating step of step (3) and passing said compressed vapors to said indirect heating step (3) for use as a source of heat therein, and
    (9) The said volatile vapors, after use as said source of heat, being recycled to some portion of the alkylation reaction system for further use therein.

2. A process as in claim 1, wherein said volatile vapors used as a source of heat in the heating step and evaporative condenser of step (3) are isoparaffinic hydrocarbon vapors normally present in at least one stage of the alkylation reaction system.

3. A process as in claim 1 wherein one source of said volatile vapors in step (8) comprises isoparaffinic hydrocarbon vapors from the overhead of said fractionation step.

4. A process as in claim 1 wherein one source of said volatile vapors in Step (8) comprises isoparaffinic hydrocarbon vapors separated from the reaction step.

5. A process as in claim 1 wherein one source of said volatile vapors in Step (8) comprises closed cycle refrigeration vapors used in indirect heat exchanging of the reaction system.

6. A process as in claim 1 wherein one source of said volatile vapors in Step (8) comprises closed cycle refrigeration vapors used in condensing isoparaffinic hydrocarbon vapors in another part of the alkylation system.

7. A process as in claim 1 wherein the volatile vapors used in steps (8) and (3) comprise closed cycle refrigeration vapors used in one part of the alkylation reaction system and isoparaffinic hydrocarbon vapors from the overhead of the fractionation step.

8. A process as in claim 1 wherein the volatile vapors used as a source of heat in step (3) comprise isoparaffinic hydrocarbon vapors from a portion of the alkylation reaction step other than the fractionation step and isoparaffinic hydrocarbon vapors from the fractionation step.

9. A process as in claim 1 wherein said volatile vapors used as a source of heat in step (3) include isoparaffinic hydrocarbon vapors separated from the said hydrocarbon phase before said hydrocarbon phase is passed to said indirect heating step.

10. A process as in claim 9 wherein said volatile vapors used a source of heat in step (3) also include isoparaffinic hydrocarbon vapors from the fractionation step.

11. A process of alkylating isoparaffinic hydrocarbons with olefinic hydrocarbons in the presence of an acid catalyst, comprising the steps of:
    (1) Contacting isoparaffinic hydrocarbons with olefinic hydrocarbons in a reaction vessel in the presence of the acid catalyst and a large excess of isoparaffinic hydrocarbons,
    (2) At least substantially separating acid catalyst, reaction product and some excess isoparaffinic hydrocarbons from one another in said reaction vessel,
    (3) Separately withdrawing the acid catalyst, some excess isoparaffinic hydrocarbons in vapor form and a liquid hydrocarbon phase effluent containing reaction product and excess isoparaffinic hydrocarbons from said reaction vessel,
    (4) Passing the hydrocarbon phase effluent to an indirect heating step utilizing at least one evaporative condenser, where sufficient heat is applied thereto to evolve a substantial proportion of the excess isoparaffinic hydrocarbons therein in vapor form therefrom, (5) Passing the said heated hydrocarbon phase effluent to a flash separating step where the said substantial proportion of the excess isoparaffinic hydrocarbons are removed overhead therefrom, (6) Passing liquid bottoms from said flash separating step to a fractionation step where heat is applied thereto to evolve further isoparaffinic hydrocarbons in vapor form therefrom, (7) Removing liquid bottoms from said fractionation step largely comprising reaction product and removing same from the system, (8) Condensing the overhead isoparaffinic hydrocarbon vapors from the flash separating step and returning same in liquid form to the reaction vessel for the purpose of maintaining the large excess of isoparaffinic hydrocarbons therein, and (9) Further recycling at least a substantial proportion of the isoparaffinic hydrocarbon vapors separately removed from (a) the reaction vessel and (b) evolved from the fractionation step to the reaction vessel in liquid form for the said purpose of maintaining the large excess of isoparaffinic hydrocarbons therein,

(10) Compressing at least some of the isoparaffinic hydrocarbon vapors from one of (a) the reaction vessel and (b) the fractionation step to a temperature substantially above the temperature of the hydrocarbon phase effluent of step (3) and using said vapors as a heating medium in the heating step of step (4) and the evaporative condenser thereof before returning same to the reaction vessel in liquid form in step (9).

12. A process as in claim 11 wherein some of the isoparaffinic hydrocarbon vapors from both the reaction vessel and the fractionation step are compressed and used as a heating medium in the heating step of step (4).

13. A process as in claim 11 wherein the hydrocarbon phase effluent is neutralized before heating step (4).

14. A process as in claim 11 wherein the bottoms from the flash separating step are neutralized before passing same to the fractionation step.

15. A process of alkylating isoparaffinic hydrocarbons with olefinic hydrocarbons in the presence of an acid catalyst comprising the steps of:

(1) Contacting isoparaffinic hydrocarbons with olefinic hydrocarbons in a reaction vessel in a reaction step in the presence of the acid catalyst and a large excess of isoparaffinic hydrocarbons, (2) Withdrawing a mixture of hydrocarbons with catalyst as effluent from said reaction vessel, (3) Separating the said effluent into a acid phase and a hydrocarbon phase substantially free of catalyst in a first separating step, (4) Maintaining the reaction and first separating step under sufficient back pressure so as to keep all hydrocarbons in liquid phase, (5) Reducing the pressure on the hydrocarbon phase to refrigerate same and vaporize some of the isoparaffinic hydrocarbons therein, (6) Passing at least a portion of said pressure reduced hydrocarbon phase in indirect heat exchange with the reaction step in the reaction vessel, thus vaporizing some additional isoparaffinic hydrocarbons, (7) Separating the vaporized isoparaffinic hydrocarbons from the liquid hydrocarbons in a second separating step after the heat exchange of the reaction step, (8) Withdrawing liquid hydrocarbons from said second separating step and passing same to an indirect heating step utilizing at least one evaporative condenser where sufficient heat is applied thereto to evolve a substantial proportion of the isoparaffinic hydrocarbons therein, (9) Passing the said heating liquid hydrocarbons from said indirect heating step to a third separating step where said isoparaffinic hydrocarbons are flashed overhead therefrom,

(10) Passing liquid bottoms from said third separating step to a fractionation step where heat is applied thereto to evolve further isoparaffinic hydrocarbons in vapor form therefrom,

(11) Condensing the overhead isoparaffinic hydrocarbon vapors from the flash separating step and returning same in liquid form to the reaction vessel and step for the purpose of maintaining the large excess of isoparaffinic hydrocarbons therein,

(12) And further recycling at least a substantial proportion of the isoparaffinic hydrocarbon vapors from the second separating step and the fractionation step to the reaction vessel and step for said purpose of maintaining a large excess of isoparaffinic hydrocarbons therein,

(13) Compressing at least some of the isoparaffinic hydrocarbon vapors from one of (a) the second separating step and (b) the fractionation step to a temperature substantially above the temperature of the liquid hydrocarbons of step (7) and using said vapors as a heating medium in the heating step of step (8) and evaporative condenser thereof before returning same to the reaction vessel and step as in step (12).

16. A process as in claim 15 wherein some of the hydrocarbon vapors from both the second separating step and the fractionation step are compressed and used as the heating medium in step (8).

17. A process as in claim 15 wherein the hydrocarbon phase effluent is neutralized before heating step (8).

18. A process as in claim 15 wherein the bottoms from the flash separating step are neutralized before passing same to the fractionation step.

19. A process of alkylating isoparaffinic hydrocarbons with olefinic hydrocarbons in the presence of an acid catalyst, comprising the steps of:

(1) Contacting isoparaffinic hydrocarbons with olefinic hydrocarbons in a reaction vessel in a reaction step in the presence of the acid catalyst and a large excess of isoparaffinic hydrocarbons, (2) Withdrawing a mixture of hydrocarbons with catalyst as effluent from said reaction vessel, (3) Separating the said effluent into an acid phase and a hydrocarbon phase substantially free of catalyst in a first separating step, (4) Maintaining the reaction and first separating steps under sufficient back pressure so as to keep all hydrocarbons in liquid phase, (5) The reaction step being cooled by indirect heat exchange utilizing a closed cycle refrigeration system having refrigerant vapors cyclically compressed and condensed before passing through a back pressure valve into the indirect heat exchange relationship, (6) Passing at least a substantial portion of the hydrocarbon phase from the first separating step to an indirect heating step utilizing at least one evaporative condenser where sufficient heat is applied thereto evolve a substantial proportion of the isoparaffinic hydrocarbons therein therefrom, (7) Passing the heated liquid hydrocarbons from said indirect heating step to a second separating step where said isoparaffinic hydrocarbons are flashed overhead therefrom, (8) Passing liquid bottoms from said second separating step to a fractionation step where heat is applied thereto to evolve further isoparaffinic hydrocarbons in vapor form therefrom, (9) Condensing the overhead isoparaffinic hydrocarbon vapors from the flash separating step and returning same in liquid form to the reaction vessel and step for the purpose of maintaining the large excess of isoparaffinic hydrocarbons therein,

(10) And further recycling at least a substantial proportion of the isoparaffinic hydrocarbon vapors from the fractionation step to the reaction vessel and step for the same purpose,

(11) Compressing at least one of the isoparaffinic hydrocarbon vapors from (a) the fractionation step and (b) the refrigerant vapors from step (5) to a temperature substantially above the temperature of the hydrocarbon phase effluent of step (3) and using said vapors as a heating medium in the heating step of step (6) and evaporative condenser thereof before returning same to the reactor or closed cycle refrigeration system, respectively.

20. A process as in claim 19 wherein both a portion of the closed cycle refrigeration system vapors and the overhead isoparaffinic hydrocarbon vapors from the fractionation step are used as heating medium in the heating step (6).

21. A process as in claim 19 wherein the bottoms from the flash separating step are neutralized before passing same to the fractionation step.

22. A process of alkylating isoparaffinic hydrocarbons with olefinic hydrocarbons in the presence of an acid catalyst, comprising the steps of:

(1) Contacting isoparaffinic hydrocarbons with olefinic hydrocarbons in a reaction vessel in a reaction step in the presence of the acid catalyst and a large excess of isoparaffinic hydrocarbons, (2) Withdrawing a mixture of hydrocarbons with catalyst as effluent from said reaction vessel, (3) Separating the said effluent into an acid phase and a hydrocarbon phase substantially free of catalyst in a first separating step, (4) Maintaining the reaction and first separating steps under sufficient back pressure so as to keep all hydrocarbons in liquid phase, (5) Reducing the pressure on the hydrocarbon phase to refrigerate same and vaporize some of the isoparaffinic hydrocarbons therein, (6) Passing at least a portion of said pressure reduced hydrocarbon phase in indirect heat exchange with the reaction step in the reaction vessel, thus vaporizing some additional isoparaffinic hydrocarbons, (7) Separating the vaporized isoparaffinic hydrocarbons from the liquid hydrocarbons in a second separating step after the heat exchange of the reaction step, (8) The vaporized hydrocarbons from the second separating step condensed in indirect heat exchange by a closed cycle refrigeration system having refrigerant vapors cyclically compressed and condensed before passage through a back pressure valve in the heat exchange relationship, the said condensed hydrocarbon vapors being recyled to the reaction step, (9) Withdrawing liquid hydrocarbons from said second separating step and passing same to an indirect heating step utilizing at least one evaporative condenser where sufficient heat is applied thereto to evolve a substantial proportion of the isoparaffinic hydrocarbons therein,

(10) Passing the said heated liquid hydrocarbons from said indirect heating step to a third separating step where said isoparaffinic hydrocarbons are flashed overhead therefrom,

(11) Passing liquid bottoms from said flash separating step to a fractionation step where heat is applied thereto to evolve further isoparaffinic hydrocarbons in vapor form therefrom,

(12) Condensing the overhead isoparaffinic hydrocarbon vapors from the flash separating step and returning same in liquid form to the reaction vessel and step for the purpose of maintaining the large excess of isoparaffinic hydrocarbons therein,

(13) And further recycling at least a substantial proportion of the isoparaffinic hydrocarbon vapors from the fractionation step to the reaction vessel and step in liquid form for the same purpose,

(14) Compressing at least one of some of the isoparaffinic hydrocarbon vapors from (a) the fractionation step overhead and (b) a portion of the closed cycle refrigeration system refrigerant vapors to a temperature substantially above the temperature of the liquid hydrocarbons of step (7) and using said vapors as a heating medium in the heating step of step (9) and evaporative condenser thereof before returning same to the reaction vessel or closed cycle refrigeration system, respectively.

23. A process as in claim 22 wherein both a portion of the closed cycle refrigeration system refrigerant vapors and the hydrocarbon vapor overhead from the fractionation step are used a heating medium in step (9).

24. A process of alkylating isoparaffinic hydrocarbons with olefinic hydrocarbons in the presence of an acid catalyst, comprising the steps of:

(1) Contacting isoparaffinic hydrocarbons with olefinic hydrocarbons in a reaction vessel in a reaction step in the presence of the acid catalyst and a large excess of isoparaffinic hydrocarbons, (2) Withdrawing a mixture of hydrocarbons with catalyst as effluent from said reaction vessel, (3) Separating the said effluent into an acid phase and a hydrocarbon phase substantially free of catalyst in a first separating step, (4) Maintaining the reaction and first separating steps under sufficient back pressure to keep all hydrocarbons in liquid phase, (5) Passing at least a substantial portion of the hydrocarbon phase from the first separating step to an indirect heating step utilizing at least one evaporative condenser where sufficient heat is applied thereto to evolve a substantial proportion of the isoparaffinic hydrocarbons therein, (6) Passing the heated liquid hydrocarbons from said indirect heating step to a flash separating step where said isoparaffinic hydrocarbons are removed overhead therefrom, (7) Passing liquid bottoms from said flash separating step to a fractionating step where heat is applied thereto to evolve further isoparaffinic hydrocarbons in vapor form therefrom, (8) Condensing the overhead isoparaffinic hydrocarbon vapors from the flash separating step and returning same in liquid form to the reaction vessel and step for the purpose of maintaining the large excess of isoparaffinic hydrocarbons therein, (9) Further recycling at least a substantial proportion of the isoparaffinic hydrocarbon vapors from the fractionation step to the reaction vessel and step in liquid form for the same purpose,

(10) Compressing at least some of the isoparaffinic hydrocarbon vapors from the fractionation step to a temperature substantially above the temperature of the hydrocarbon phase effluent of step (3) and using said vapors as a heating medium in the heating step of step (5) and evaporative condenser thereof before returning same to the reaction vessel.

25. A process as in claim 24 wherein the reaction vessel and step are indirectly heat exchanged and a portion of the heat exchanging medium therefor is additionally compressed to a temperature substantially above the temperature of the hydrocarbon phase effluent of step (3) and used as a heating medium in the heating step of step (5).

26. A process as in claim 24 wherein said hydrocarbon phase is neutralized before passing same to said indirect heating step.

27. A process as in claim 24 wherein the liquid bottoms from the flash separating step are neutralized before passing same to said fractionation step.

* * * * *